US 6,699,659 B2

(12) United States Patent
Webster

(10) Patent No.: US 6,699,659 B2
(45) Date of Patent: *Mar. 2, 2004

(54) PRODUCTS AND METHODS FOR ANALYZING NUCLEIC ACIDS INCLUDING IDENTIFICATION OF SUBSTITUTIONS, INSERTIONS AND DELETIONS

(75) Inventor: Teresa A. Webster, Loma Mar, CA (US)

(73) Assignee: Affymetrix, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 16 days.

(21) Appl. No.: 09/217,368

(22) Filed: Dec. 21, 1998

(65) Prior Publication Data

US 2001/0049095 A1 Dec. 6, 2001

Related U.S. Application Data

(60) Provisional application No. 60/087,567, filed on Jun. 1, 1998.

(51) Int. Cl.[7] .......................... C12Q 1/68; G01N 33/48; G06F 19/00
(52) U.S. Cl. ................... 435/6; 702/19; 702/20
(58) Field of Search .................. 435/6; 436/501; 536/23.1, 24.1, 24.3–24.33; 702/19, 20

(56) References Cited

U.S. PATENT DOCUMENTS

| 5,202,231 A | 4/1993 | Drmanac .................. 435/6 |
| 5,525,464 A | 6/1996 | Drmanac et al. ........... 435/6 |
| 5,700,637 A | 12/1997 | Southern ................. 435/6 |
| 5,733,729 A | 3/1998 | Lipshutz et al. ........... 435/6 |
| 5,795,716 A | 8/1998 | Chee et al. ............... 435/6 |
| 5,871,928 A | 2/1999 | Fodor et al. .............. 435/6 |
| 5,974,164 A | 10/1999 | Chee ..................... 382/129 |
| 6,027,880 A * | 2/2000 | Cronin et al. ............. 435/6 |

FOREIGN PATENT DOCUMENTS

| EP | 0717113 A2 | 6/1996 | ............ C12Q/1/68 |
| EP | 0785280 A2 | 7/1997 | ............ C12Q/1/68 |
| WO | 92/10588 | 6/1992 | |
| WO | 95/00530 | 1/1995 | |
| WO | WO 95/11995 | 5/1995 | ............ C12Q/1/68 |
| WO | WO 97/29212 | 8/1997 | ............ C12Q/1/68 |
| WO | WO 99/09218 | 2/1999 | ............ C12Q/1/68 |

OTHER PUBLICATIONS

Conner et al., "Detection of Sickle Cell $\beta^S$–globin Allele by Hybridization with Synthetic Oligonucleotides." Proceeding of the National Academy of Sciences USA. Jan. 1983, vol. 80, pp. 278–282.

Southern, E. M., Maskos, U., Elder, J.K., "Analyzing and Comparing Nucleic Acid Sequences by Hybridization to Arrays of Oligonucleotides: Evaluation Using Experimental Models", Department of Biochemistry, University of Oxford, UK, Dec. 26, 1991.

(List continued on next page.)

Primary Examiner—Ardin H. Marschel
(74) Attorney, Agent, or Firm—Ritter, Lang & Kaplan LLP

(57) ABSTRACT

Systems and methods for detecting monomer changes in a sample when an unknown quantity of expected monomers may also be present. Homogeneous and heterogeneous samples are exposed to polymer probes for hybridization. The hybridization affinities of the polymer probes to the samples are then compared to determine differences between the polymers in the samples. Accordingly, deletion, substitution and insertion mutations may be detected in a heterogeneous sample of nucleic acids.

9 Claims, 22 Drawing Sheets

OTHER PUBLICATIONS

Hacia et al., "Detection of heterozygous mutations in BRCA1 using high density oligonucleotide arrays and two-colour fluorescence analysis", 1996, Nature Genetics, vol. 14, No. 4.

Chee et al., "Accessing genetic information with high-density DNA arrays", 1996, Science, vol. 274., pp. 610–614.

Lipshutz et al., "Using oligucleotide probe arrays to access genetic diversity", Biotechniques, vol. 19, No. 3., pp. 442–447, 1995.

Fan et al., "Genetic mapping: Finding and analyzing single-nucleotide polymorphisms with high-density DNA arrays", 1997, American Journal of Human Genetics, vol. 61, No. 4, Suppl.

* cited by examiner

FORMULAS

All types of intensity values will have the name $Int<Type>$. The definitions of all intensity types are given below in the section Intensity Abbreviations.

Intensity Abbreviations
The following intensities are background subtracted and normalized.
(See formula for $Int$ under Normalization below)
$IntUK_i$ = The intensity of probe$_i$ where the probe set is from the Unknown Intensity Data.

$IntRef_i$ = The intensity of probe$_i$, where the probe set is from the Reference Intensity Data.

$IntUK_{wt}$ = The intensity of the wildtype or perfect match probe, where the probe set is from the Unknown Intensity Data.

$IntRef_{wt}$ = The intensity of the wildtype or perfect match probe, where the probe set is from the Reference Intensity Data.

$IntUK_{mut}$ = The intensity of the *putative mutant* probe (see Mutant Filter Section), where the probe set Is from the Unknown Intensity Data.

$IntRef_{mut}$ = The intensity of the *putative mutant* probe see Mutant Filter Section), where the probe set Is from the Reference Intensity Data.

$IntRef_{del}$ = The intensity of the deletion probe, where the probe set is from the Reference Intensity Data.

$IntUK_{del}$ = The intensity of the deletion probe, where the probe set is from the Unknown Intensity Data.

The following intensities are NOT background subtracted and normalized
$IntBkg$ = Intensity of the empty cel (no probe present) that is grouped with the 4 cels of a probe set.
$IntA$ = Mean intensity of the probe with an "A" in the substitution position of a probe set.
$IntC$ = Mean intensity of the probe with a "C" in the substitution position of a probe set.
$IntG$ = Mean intensity of the probe with a "G" in the substitution position of a probe set.
$IntT$ = Mean intensity of the probe with a "T" in the substitution position of a probe set.
$IntRaw_{wt}$ = Mean intensity of the wildtype of perfect match probe in a given probe set.
$IntRaw_{nonwt}$ = Mean intensity of probe$_i$ in a given probe set, where the probe is not the wildtype probe.

FIG. 20A

Normalization

Intensities of probe sets for each exon in the unknown sample are normalized relative to the intensities of the same probe sets with the reference samples.

$RefVectorMag$= For a given probe set with the Reference sample :
$$\sqrt{IntA^2 + IntC^2 + IntG^2 + IntT^2}$$
$UKVectorMag$= For a given probe set with the Unknown sample :
$$\sqrt{IntA^2 + IntC^2 + IntG^2 + IntT^2}$$
$NumExonSense$= The number of standard and standard varient sense probe sets that cover all sites in a given exon.
$NumExonAntiSense$= The number of standard and standard varient antisense probe sets that cover all sites in a given exon.

$$ExonSenseNorm = \left( \sum_{i=1}^{i=NumExonSense} (RefVectorMag / UKVectorMag) \right) / NumExonSense$$

$$ExonAntiSenseNorm = \left( \sum_{i=1}^{i=NumExonAntiSense} (RefVectorMag / UKVectorMag) \right) / NumExonAntiSense$$

$Int$ = NormFactor * (Mean Cel Intensity - Bkg), where the minimum value = 1;
  IF the Mean Cel Intensity is from the reference sample
    THEN NormFactor= 1

ELSE IF Mean Cel Intensity is from the unkown sample AND
      Probe is from a Sense ProbeSet
   THEN
     NormFactor = $ExonSenseNorm$ for the given exon ELSE IF Mean Cel Intensity is from the unknown sample AND
      Probe is from an AntiSense ProbeSet
   THEN
     NormFactor = $ExonAntiSenseNorm$ for the given exon

FIG. 20B

DiscQualityFilter $NumPS$ = The number of standard and standard varient probe sets in a given exon minus *outlyer probe sets*.

*Outlyer probe set*= Probe set, where *mean intensitiy - bkg* $< 0$, for any of the A,C,G, or T substituted cels in the probe set. That is, all intensities of the cels in the probe set must be above the background, in order to include the probe set in the computation of *DiscQualityFilter*.

$$IntDiscPS = (\text{Mean Int. Wildtype Probe} - bkg) / (1/3) \sum_{I=1}^{i=3 \text{ substitution probes}} (\text{Mean Intensity NonWildtype Probe}_i - bkg)$$

$$DiscQualityFilter = (\sum_{I=1}^{i=NumPS} IntDiscPS_i) / NumPS$$

RefMaxInt & UkMaxInt

IF $IntBkg$ > $OutlverBkg$
  THEN $IntBkg = 0$.

$RefMaxInt$ = Max($IntA$- $IntBkg$, $IntC$- $IntBkg$, $IntG$- $IntBkg$, $IntG$- $IntBkg$), where the probe set is from the Reference Intensity Data.

$UKMaxInt$ = Max($IntA$- $IntBkg$, $IntC$- $IntBkg$, $IntG$- $IntBkg$, $IntG$- $IntBkg$), where the probe set is from the Unknown Intensity Data.

$RefIntDisc$ =
$$IntRaw_{wt} / (1/3) \sum_{I=1}^{i=3 \text{ substitution probes}} IntRaw_{nonwti}$$, where the probe set is from the reference intensity data VectorRatio $RefVectorMag$= sqrt($IntA^2 + IntC^2 + IntG^2 + IntT^2$), where the probe set is from the Reference intensity Data.

$NormUKVectorMag$= sqrt($Norm^2 (IntA^2 + IntC^2 + IntG^2 + IntT^2)$), where the probe set is from the Unknown Intensity Data, and
  where $Norm$ = $ExonAntiSenseNorm$, given an antisense probe set or
    $Norm$= $ExonSenseNorm$, given a sense probe set,
  see Normalization.

$VectorRatio$ = $RefVectorMag / NormUKVectorMag$ mutRatio
For a given substitution probe$_i$, that is not the wildtype probe. in a given probe set,
$mutRatio_i$ = $((IntRef_{wt} / IntRef_i) - (IntUK_{wt} / IntUK_i))/(IntRef_{wt} / IntRef_i)$ delRatio =
  $((IntRef_{wt} / IntRef_{del}) - (IntUK_{wt} / IntUK_{del}))/(IntRef_{wt} / IntRef_{del})$

FIG. 20C

SubstitutionScore

*TilePair* = A pair of SENSE and ANTISENSE tiles that share all other properties in common, except for the strand that is covered.
*NumTilePairs*= The number of redundant TilePairs, STANDARD and STANDARD VARIANT, that cover a postion.

*SenseMixtureVariableScore = dot metric + DNeighborRatio + dratio + rank*,
    where the mixture variables are computed for a given SENSE probe set.

*AntiSenseMixtureVariableScore = dot metric + DNeighborRatio + dratio + rank*,
    where the mixture variables are computed for a given ANTISENSE probe set.

```
IF Probe Set (where Type= SENSE or ANTISENSE)
    1) Calls the putative mutant based on MutantFilterTest₂ (Fig.3) AND
    2) Passes Single Site Quality Test
   THEN Count<Type>ProbeSet
ELSE
     DoNotCount<Type>ProbeSet
```

For the SENSE and ANTISENSE Probe Sets that a comprise a TilePair at Site$_i$,
IF DoNotCountSENSEProbeSet AND DoNotCountANTISENSEProbeSet
    THEN *TileScore$_i$* = 0
ELSE IF  CountSENSEProbeSet AND DoNotCountANTISENSEProbeSet
    THEN *TileScore$_i$* = *SenseMixtureVariableScore*
ELSE IF DoNotCountSENSEProbeSet AND CountANTISENSEProbeSet
    THEN *TileScore$_i$* = *AntiSenseMixtureVariableScore*
ELSE IF CountSENSEProbeSet AND CountANTISENSEProbeSet AND
        *TilePairDM > sameAtomPairDMmax*
    THEN *TileScore$_i$* = *AntiSenseMixtureVariableScore + SenseMixtureVariableScore*
ELSE IF CountSENSEProbeSet AND CountANTISENSEProbeSet AND
        *TilePairDM <= sameAtomPairDMmax*
    THEN *TileScore$_i$* = 0

$$SubstitutionScore = \sum_{i=1}^{i=NumTilePairs} TileScore_i$$

Deletion Score

*ProbeSetScore = dot metric + dratio*

$$DeletionScore = \sum_{i=1}^{i=Number\ of\ probe\ sets\ that\ passed\ the\ Single\ Site\ Mutation\ filter} ProbeSetScore_i$$

FIG. 20D dot metric

IF *dot metric* is for "Test for Substitution Mutation (Fig. 16)"
    THEN N = 4 substitution cels $(A, C, G, T)$
ELSE IF *dot metric* is for "Test for Deletion Mutation (Fig. 15)"
    THEN N = 5 cels $(A, C, G, T,$ and single base deletion probe$)$ $nIntUK_i = IntUK_i / IntUK_{wt}$
$nIntRef_i = IntRef_i / IntRef_{wt}$ $$sxx = \sum_{i=1}^{N\ cels} (nIntUK_i \cdot nIntUK_i) / (nIntUK_{wt} \cdot nIntUK_{wt})$$

$$sxy = \sum_{i=1}^{N\ cels} (nIntUK_i \cdot nIntRef_i) / (nIntUK_{wt} \cdot nIntRef_{wt})$$

$$syy = \sum_{I=1}^{N\ cels} (nIntRef_i \cdot nIntRef_i) / (nIntRef_{wt} \cdot nIntRef_{wt})$$

*dot metric* = $1 - \mathrm{sqrt}(sxy/(sxx * syy))$

TilePairDM

*TilePairDM = dotmetric*,
where for SENSE and ANTISENSE Probe Sets that comprise the same Tile Pair at $site_i$
$nIntUK_i = IntSenseProbe_i / IntSenseProbe_{wt}$
$nIntRef_i = IntAntiSenseProbe_i / IntAntiSense_{wt}$ dRatio $IntRef_{p3\ x\ p4}$ = The product of the intensities of the two subsitution probes that are neither the wildtype probe or the putative mutant probe, in the given probe set with the reference sample.

$IntUK_{p3\ x\ p4}$ = The product of the intensities (Int) of the two subsitution probes that are neither the wildtype probe or the putative mutant probe, in the given probe set with the unknown sample.

$N1_{Ref} = (IntRef_{wt} - \mathrm{sqrt}(IntRef_{p3\ x\ p4})) / (IntRef_{Mut} - \mathrm{sqrt}(IntRef_{p3\ x\ p4}))$ $N1_{UK} = (IntUK_{wt} - \mathrm{sqrt}(IntUK_{p3\ x\ p4})) / (IntUK_{Mut} - \mathrm{sqrt}(IntUK_{p3\ x\ p4}))$

*dratio* = $(N1_{Ref} - N1_{UK}) / N1_{Ref}$

FIG. 20E dNeighborRatio:

The *dNeighborRatio* is computed using only probe sets (SENSE and ANTISENSE) that comprise the STANDARD tiles. Probe sets from STANDARD VARIENT tiles are not used.

i = The probe set that covers the ith site (a neighbor probe set), relative to the current probe $set_0$; where the current probe $set_0$ covers the current $site_0$. A neighbor probe set must cover the same strand (SENSE or ANTISENSE) as does probe $set_0$.

IF $IntUK_{wti} / IntUK_{Mut0}$ < $IntRef_{wti} / IntRef_{Mut0}$
  THEN $dNRVal_i$ = +*NRVal*
ELSE
  $dNRVal_i$ = −*NRVal*

$$DNeighborRatio = \sum_{i=-2,\ i<>0}^{i=2} d\,NRVal_i$$

IF the current $site_0$ does not have two nieghbors on each site
  THEN
*DNeighborRatio* = 0 rank:

For a given probe set,
If the probe (A,C,G,T, or deletion) that gives the maximum *IntUK* =
  the probe that gives the maximum *IntRef*
  THEN *rank* = 0.
ELSE  *rank* = 1.

FIG. 20F

Make Putative Mutant Call- Test$_1$

IF *Number Good Probe Sets* (defined in step 353 of Fig. 13) is between 1 & 2 AND
(*mutRatioDiff* < 0.190   AND  1*mutRatio$_i$* < *MutRatioCut*)  OR
1*mutRatio$_i$* < 0.330
   THEN *Putative Mutant Call* = "N" (no call)

ELSE IF *mutRatioDif* < 0.99 AND 1*mutRatio$_i$* < *MutRatioCut*
   THEN *Putative Mutant Call* = "N" (no call)

ELSE
   Putative Mutant Call = Substitution Base of Probe$_i$

Make Putative Mutant Call- Test$_2$

IF 1*mutRatio$_i$* = 0.0
   THEN *Putative Mutant Call* = "N" (no call)

ELSE
   Putative Mutant Call = Substitution Base of Probe$_i$

FIG. 20G

PRODUCTS AND METHODS FOR ANALYZING NUCLEIC ACIDS INCLUDING IDENTIFICATION OF SUBSTITUTIONS, INSERTIONS AND DELETIONS

This application claims the benefit of U.S. Provisional Application No. 60/087,567, filed Jun. 1, 1998, which is hereby incorporated by reference.

GOVERNMENT RIGHTS NOTICE

Portions of the material in this specification arose under the cooperative agreement 70NANB5H1031 between Affymetrix, Inc. and the Department of Commerce through the National Institute of Standards and Technology.

BACKGROUND OF THE INVENTION

The present invention is related to computer systems for analyzing polymers. More particularly, the invention provides systems and methods for analyzing biopolymers, such as nucleic acids, in order to identify monomer substitutions, insertions and deletions.

U.S. Pat. No. 5,424,186, which is hereby incorporated by reference for all purposes, describes pioneering techniques for, among other things, forming and using high density arrays of molecules such as oligonucleotides, peptides, polysaccharides, and other materials. Arrays of oligonucleotides, for example, are formed on the surface by sequentially removing a photoremovable group from a surface, coupling a monomer to the exposed region of the surface, and repeating the process. These techniques have been used to form extremely dense arrays of oligonucleotides, peptides, and other materials. Such arrays are useful in, for example, drug development, oligonucleotide sequencing, oligonucleotide sequence checking, and a variety of other applications. The synthesis technology associated with this invention has come to be known as "VLSIPS" or "Very Large Scale Immobilized Polymer Synthesis" technology.

Additional techniques for forming and using such arrays are described in U.S. Pat. No. 5,384,261, which is also incorporated by reference for all purposes. Such techniques include systems for mechanically protecting portions of a substrate (or chip), and selectively deprotecting/coupling materials to the substrate. These techniques are now known as "VLSIPS II." Still further techniques for array synthesis are provided in U.S. application Ser. No. 08/327,512, also incorporated herein by reference for all purposes.

Dense arrays fabricated according to these techniques are used, for example, to screen the array of probes to determine which probe(s) are complementary to a target of interest. According to one specific aspect of the inventions described above, the array is exposed to a labeled target. The target may be labeled with a wide variety of materials, but an exemplary label is a fluorescein label. The array is then scanned with a confocal microscope based detection system, or other related system, to identify where the target has bound to the array. Other labels include, but are not limited to, radioactive labels, large molecule labels, and others.

Innovative computer-aided techniques for identifying monomers in sample polymers are disclosed in U.S. patent application Ser. No. 08/531,137 (attorney docket no. 16528X008210), No. 08/528,656 (attorney docket no. 16528X-017600), and No. 08/618,834 (attorney docket no. 16528X-016400), which are all hereby incorporated by reference for all purposes. However, improved systems and methods are still needed to evaluate, analyze, and process the vast amount of information now used and made available by these pioneering technologies.

One area that can be more thoroughly explored is identifying changes in a heterogeneous sample of polymers. For example, biopsies from cancerous areas or tumors of a patient's body will typically include genetic material from both normal cells and cancerous cells. In order to better diagnose a cancerous area, it would be beneficial to be able to identify mutations in the p53 genes of a heterogeneous sample, especially where an unknown quantity of wild-type p53 genes are present.

SUMMARY OF THE INVENTION

The present invention provides techniques for detecting monomer changes in a heterogeneous sample when an unknown quantity of expected (e.g., wild-type) monomers may also be present. Heterogeneous and homogenous samples are exposed to polymer probes for hybridization, where the homogeneous sample acts as a reference. The hybridization affinities of the polymer probes to the heterogeneous and homogeneous samples are then compared to determine differences between the polymers in the samples. For example, embodiments of the invention allow for the detection of deletion, substitution and insertion mutations in a heterogeneous samples of nucleic acids. Several embodiments of the invention are as follows.

In one embodiment of the invention, a method of analyzing a heterogeneous sample of nucleic acids is provided. Hybridization affinities of a homogeneous sample of nucleic acids to a plurality of nucleic acid probes are received. Hybridization affinities of the heterogeneous sample of nucleic acids to the plurality of nucleic acid probes are also received. The hybridization affinities of the homogeneous and heterogeneous samples are then compared to identify a mutation in the heterogeneous sample. In a preferred embodiment, a first ratio of a hybridization affinity of a non-wild-type probe to a hybridization affinity of a wild-type probe for the homogeneous sample of nucleic acids is calculated and a second ratio of a hybridization affinity of a non-wild-type probe to a hybridization affinity of a wild-type probe for the heterogeneous sample of nucleic acids is calculated. A mutation is identified in the heterogeneous sample if the first ratio is less than the second ratio.

In another embodiment of the invention, a method of analyzing a heterogeneous sample of nucleic acids is provided. Hybridization affinities of a homogeneous sample of nucleic acids to a plurality of nucleic acid probes are received. The plurality of nucleic acid probes include a wild-type probe and at least one non-wild-type probe. Hybridization affinities of a heterogeneous sample of nucleic acids to the plurality of nucleic acid probes are also received. A first ratio of a hybridization affinity of a wild-type probe to a hybridization affinity of a non-wild-type probe for the homogeneous sample of nucleic acids is calculated. A second ratio of a hybridization affinity of a wild-type probe to a hybridization affinity of a non-wild-type probe for the heterogeneous sample of nucleic acids is calculated. A third ratio of the difference between the first and second ratios to the first ratio is then calculated. It is determined that there is a mutation in the heterogeneous sample if the third ratio is above a predetermined threshold, the mutation being identified by the non-wild-type probe.

A further understanding of the nature and advantages of the inventions herein may be realized by reference to the remaining portions of the specification and the attached drawings.

BRIEF DESCRIPTION OF THE DRAWINGS

FIGS. 20A–20G show formulas that are utilized in a preferred embodiment.

DETAILED DESCRIPTION OF PREFERRED EMBODIMENTS

The present invention provides innovative systems and methods of analyzing polymers. In the description that follows, the invention will be described in reference to a preferred embodiment that identifies nucleotide mutations such as substitutions, insertions or deletions, such as in the p53 gene. However, the invention may be advantageously applied to other polymers including peptides, polysaccharides, and the like for various applications. Accordingly, the description is provided for purposes of illustration and not for limiting the spirit and scope of the invention.

Figure 1:
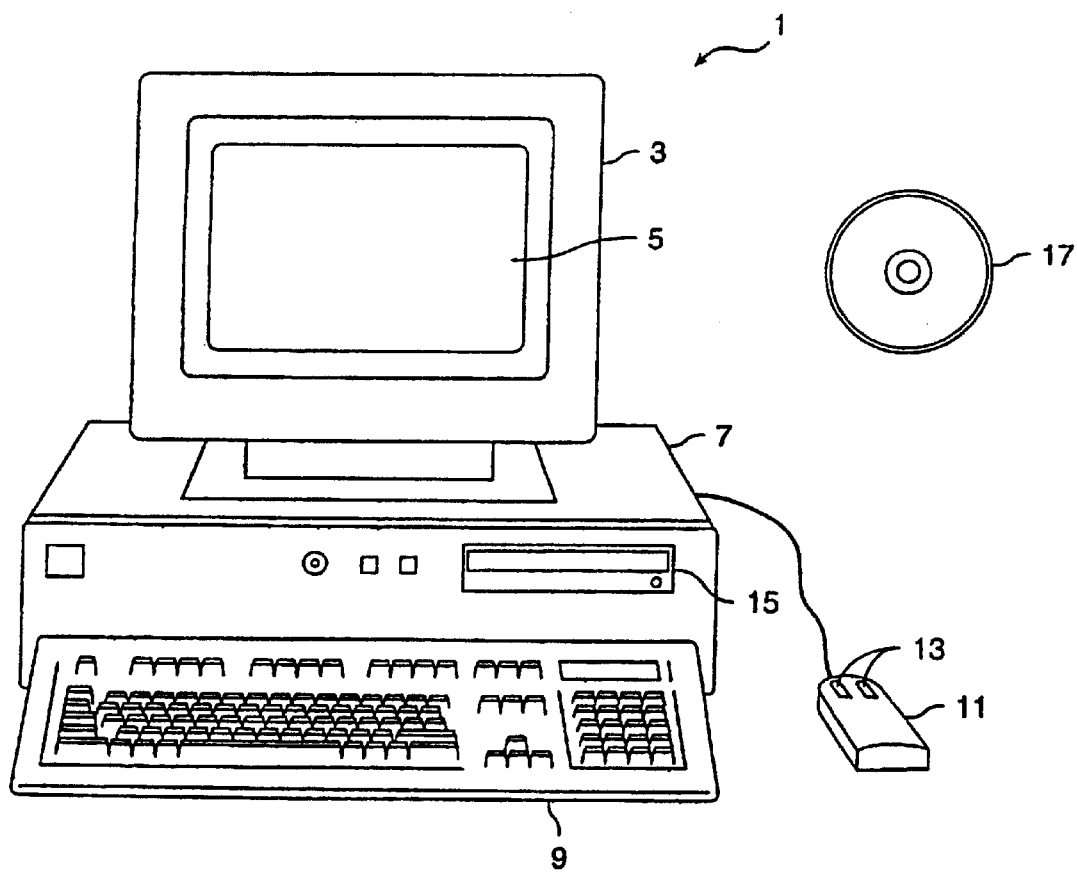
FIG. 1 illustrates an example of a computer system that may be used to execute software embodiments of the present invention.

FIG. 1 illustrates an example of a computer system that may be used to execute software embodiments of the present invention. FIG. 1 shows a computer system 1 that includes a monitor 3, screen 5, cabinet 7, keyboard 9, and mouse 11. Mouse 11 may have one or more buttons such as mouse buttons 13. Cabinet 7 houses a CD-ROM drive 15 and a hard drive (not shown) that may be utilized to store and retrieve software programs including computer code incorporating the present invention or data for use with the invention. Although a CD-ROM 17 is shown as the computer readable medium, other computer readable media including floppy disks, DRAM, hard drives, flash memory, tape, and the like may be utilized. Cabinet 7 also houses familiar computer components (not shown) such as a processor, memory, and the like.

Figure 2:
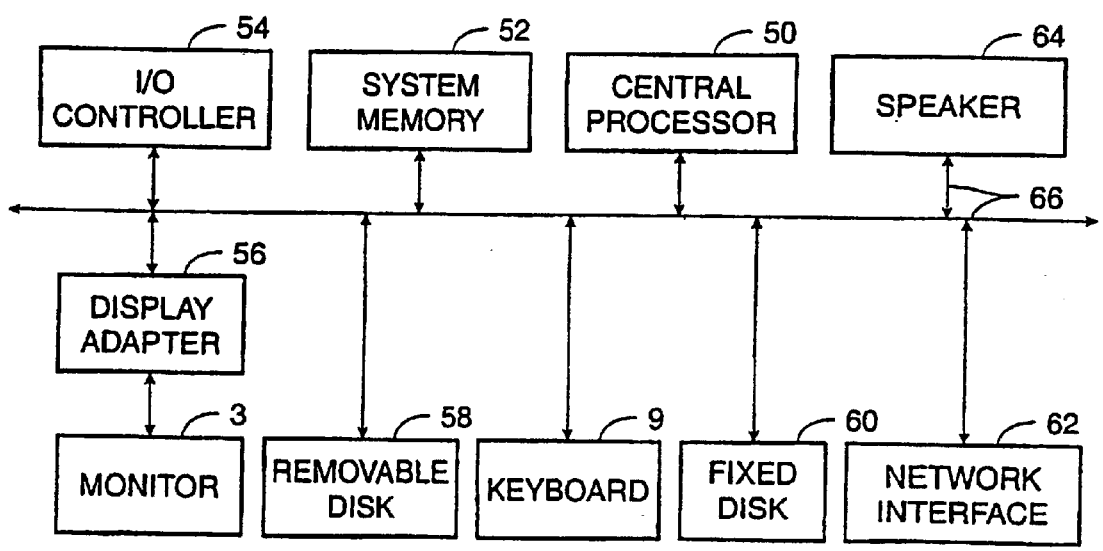
FIG. 2 shows a system block diagram of a typical computer system.

FIG. 2 shows a system block diagram of computer system 1 used to execute software embodiments of the present invention. As in FIG. 1, computer system 1 includes monitor 3 and keyboard 9. Computer system 1 further includes subsystems such as a central processor 50, system memory 52, I/O controller 54, display adapter 56, removable disk 58, fixed disk 60, network interface 62, and speaker 64. Removable disk 58 is representative of removable computer readable media like floppies, tape, CD-ROM, removable hard drive, flash memory, and the like. Fixed disk 60 is representative of an internal hard drive or the like. Other computer systems suitable for use with the present invention may include additional or fewer subsystems. For example, another computer system could include more than one processor 50 (i.e., a multi-processor system) or memory cache.

Arrows such as 66 represent the system bus architecture of computer system 1. However, these arrows are illustrative of any interconnection scheme serving to link the subsystems. For example, display adapter 56 may be connected to central processor 50 through a local bus or the system may include a memory cache. Computer system 1 shown in FIG. 2 is but an example of a computer system suitable for use with the present invention. Other configurations of subsystems suitable for use with the present invention will be readily apparent to one of ordinary skill in the art. In one embodiment, the computer system is a workstation from Sun Microsystems.

The VLSIPS™ technology provides methods of making very large arrays of oligonucleotide probes on very small chips. See U.S. Pat. No. 5,143,854 and PCT patent publication Nos. WO 90/15070 and 92/10092, each of which is hereby incorporated by reference for all purposes. The oligonucleotide probes on the chip are used to detect complementary nucleic acid sequences in a sample nucleic acid of interest (the "target" nucleic acid).

The present invention provides methods of analyzing hybridization affinity or intensity data for a chip including probes that has been exposed to a labeled polymer. In a representative embodiment, the data represent fluorescence intensity from a biological array, but the data may also represent other data such as radioactive intensity. Therefore, the present invention is not limited to analyzing fluorescent measurements of hybridization but may be readily utilized to analyze other measurements of hybridization.

For purposes of illustration, a computer system that designs a chip mask, synthesizes the probes on the chip, labels the nucleic acids, and scans the hybridized nucleic acid probes will be described. Such a system is fully described in U.S. patent application Ser. No. 08/249,188, which is hereby incorporated by reference for all purposes. The present invention may be used within such a system, in another system, or separately for analyzing data, such as at remote locations.

Figure 3:
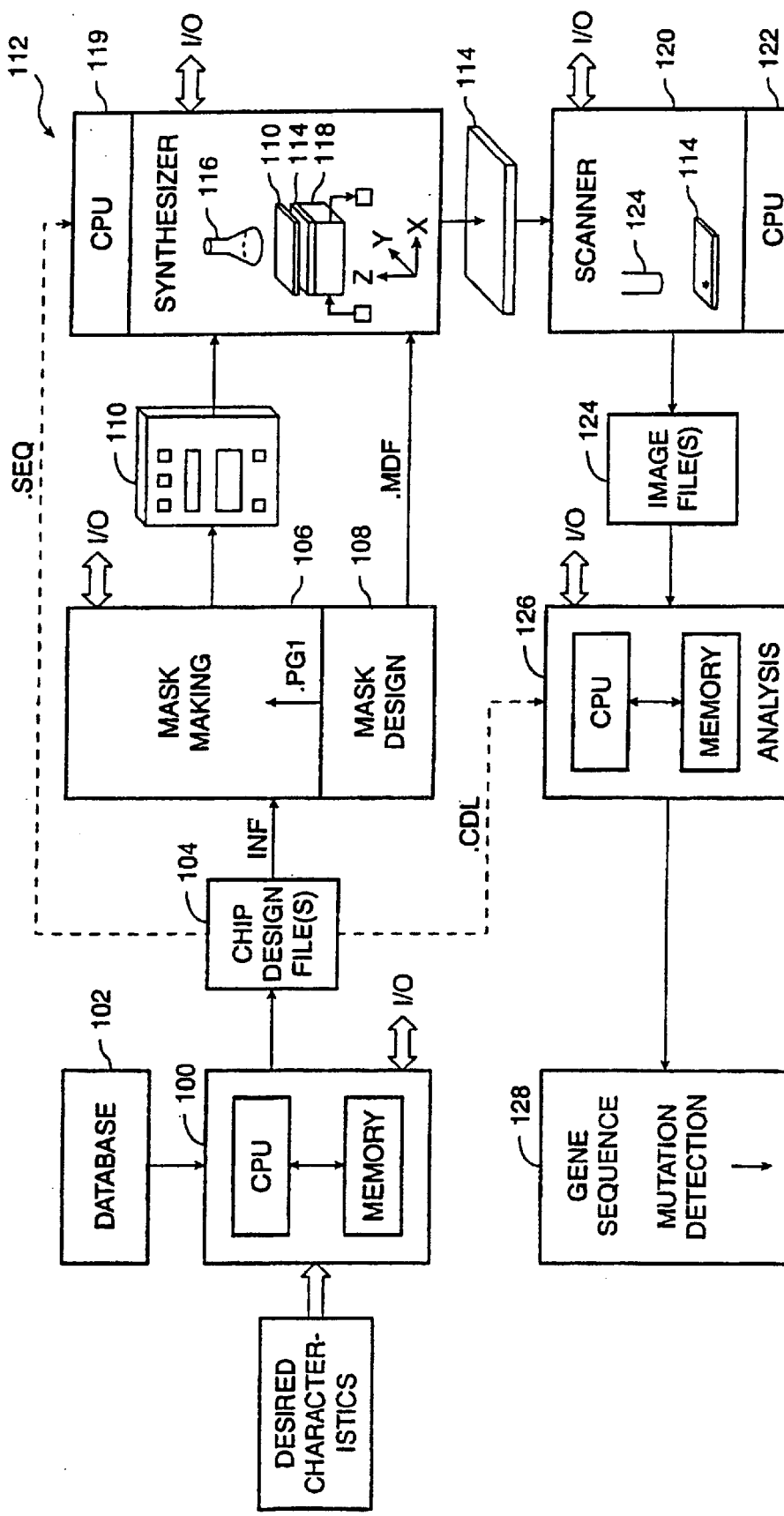
FIG. 3 illustrates an overall system for forming and analyzing arrays of biological materials such as DNA or RNA.

FIG. 3 illustrates a computerized system for forming and analyzing arrays of biological materials. A computer 100 is used to design arrays of biological polymers such as RNA or DNA. The computer may be, for example, an appropriately programmed IBM compatible personal computer running Windows NT including appropriate memory and a CPU as shown in FIGS. 1 and 2. Computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of computer system 100 is a set of chip design computer files 104 in the form of, for example, a switch matrix, as described in PCT application WO 92/10092, and other associated computer files.

The chip design files are provided to a system or process 106 that designs the lithographic masks used in the fabrication of arrays of molecules such as DNA. System or process 106 may include the hardware necessary to manufacture masks 110 and also the necessary computer hardware and software 108 necessary to lay the mask patterns out on the mask in an efficient manner. As with the other features in FIG. 3, such equipment may or may not be located at the same physical site, but is shown together for ease of illustration in FIG. 3. System or process 106 generates masks 110 or other synthesis patterns such as chrome-on-glass masks for use in the fabrication of polymer arrays.

Masks 110, as well as selected information relating to the design of the chips from computer system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical reagents are directed through flow cell 118 for coupling to deprotected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked targets. The targets may or may not be complementary to one or more of the molecules on the substrate. The targets are marked with a label such as a fluorescein label (indicated by an asterisk in FIG. 3) and placed in a scanning system 120. Scanning system 120 again operates under the direction of an appropriately programmed digital computer 122, which also may or may not be the same computer as the computers used in synthesis, mask making, and mask design.

Scanner 120 includes a detection device 124 such as a confocal microscope or CCD (charge-coupled device) that is used to detect the location where labeled target (*) has bound to the substrate. The output of scanner 120 is an image file(s) 124 indicating, in the case of fluorescein labeled target, the fluorescence intensity (photon counts or other related measurements, such as voltage) as a function of position on the substrate. Since higher photon counts will be observed where the labeled target has bound more strongly to the array of polymers, and since the monomer sequence of the polymers on the substrate is known as a function of position, it becomes possible to determine the sequence(s) of polymer(s) on the substrate that are complementary to the target.

Image file 124 may be provided as input to an analysis system 126 that incorporates embodiments of the present invention. Again, the analysis system may be any one of a wide variety of computer system. The present invention provides systems and methods of analyzing hybridization data, which may include chip design files and image files, and providing appropriate output 128. As an example, the present invention may be used to determine the position of mutations in a sample of DNA or RNA.

Figure 4:
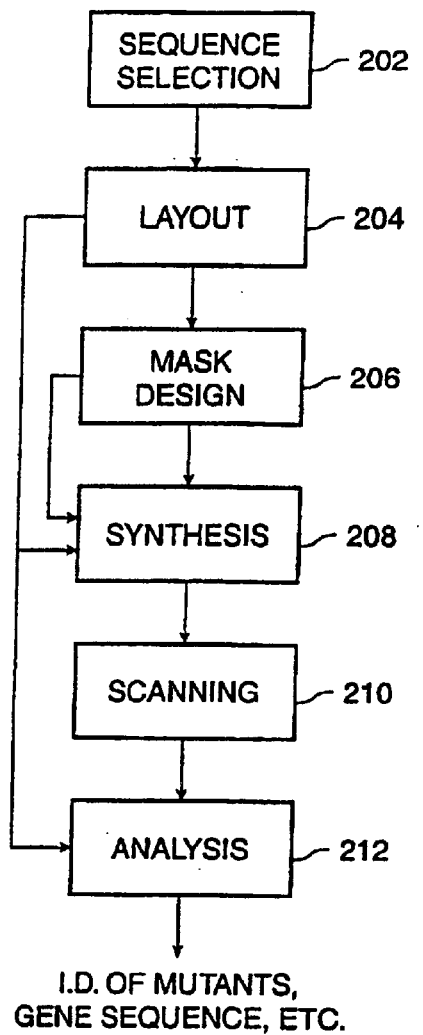
FIG. 4 is an illustration of an embodiment of software for the overall system.

FIG. 4 provides a simplified illustration of the overall software system used in the operation of one embodiment of the invention. As shown in FIG. 4, the system first identifies the genetic sequence(s) or targets that would be of interest in a particular analysis at a step 202. The sequences of interest may, for example, be normal or mutant portions of a gene, genes that identify heredity, provide forensic information, genes for cancer detection, or pathology. Sequence selection may be provided via manual input of text files or may be from external sources such as GenBank. At a step 204 the system evaluates the gene to determine or assist the user in determining which probes would be desirable on the chip, and provides an appropriate "layout" on the chip for the probes.

The chip usually includes probes that are complementary to a reference nucleic acid sequence, which has a known sequence. A wild-type probe is a probe that will ideally hybridize with the reference sequence and thus a wild-type gene (also called the chip wild-type) would ideally hybridize with wild-type probes on the chip. The sample or target sequence is typically similar to the reference sequence except for the presence of substitutions, insertions, deletions, and the like. The layout implements desired characteristics such as arrangement on the chip that permits "reading" of genetic sequence and/or minimization of edge effects, ease of synthesis, and the like.

Figure 5:
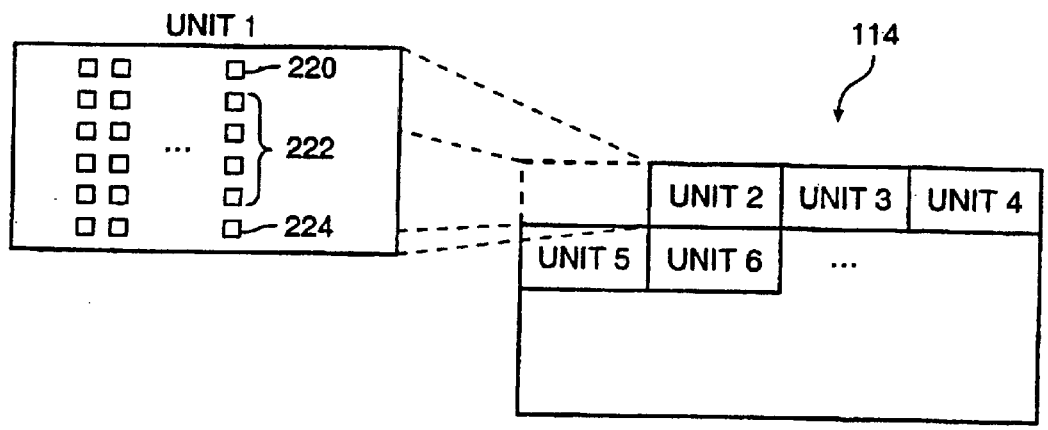
FIG. 5 illustrates the global layout of a chip formed in the overall system.

In order to better understand a layout of a chip, FIG. 5 illustrates the global layout of a chip. Chip 114 is composed of multiple units where each unit may contain different tilings for the wild-type sequence or multiple wild-type sequences. Unit 1 is shown in greater detail and shows that each unit is composed of multiple cells, which are areas on the chip that may contain probes. Conceptually, each unit includes multiple sets of related cells. As used herein, the term "cell" refers to a region on a substrate that contains many copies of a molecule or molecules (e.g., nucleic acid probes).

Each unit is composed of multiple cells that may be placed in rows (or "lanes") and columns. In one embodiment, a set of five related cells includes the following: a wild-type cell 220, "mutation" cells 222, and a "blank" cell 224. Cell 220 contains a wild-type probe that is the complement of a portion of the wild-type sequence. Cells 222 contain "mutation" probes for the wild-type sequence. For example, if the wild-type probe is 3'-ACGT, the probes 3'-ACAT, 3'-ACCT, 3'-ACGT, and 3'-ACTT may be the "mutation" probes. Cell 224 is the "blank" cell because it contains no probes (also called the "blank" probe). As the blank cell contains no probes, labeled targets should not bind to the chip in this area. Thus, the blank cell provides an area that can be used to measure the background intensity. In preferred embodiments, there is only one cell for the wild-type probes.

Referring again to FIG. 4, at a step 206 the masks for the synthesis are designed. At a step 208 the software utilizes the mask design and layout information to make the DNA or other polymer chips. This software 208 will control, among other things, relative translation of a substrate and the mask, the flow of desired reagents through a flow cell, the synthesis temperature of the flow cell, and other parameters. At a step 210, another piece of software is used in scanning a chip thus synthesized and exposed to a labeled target. The software controls the scanning of the chip, and stores the data thus obtained in a file that may later be utilized to extract sequence information.

At a step 212 a computer system utilizes the layout information and the fluorescence information to evaluate the hybridized nucleic acid probes on the chip. Among the important pieces of information obtained from DNA chips are the identification of mutant targets and determination of genetic sequence of a particular target.

Figures 6, 7, 8:
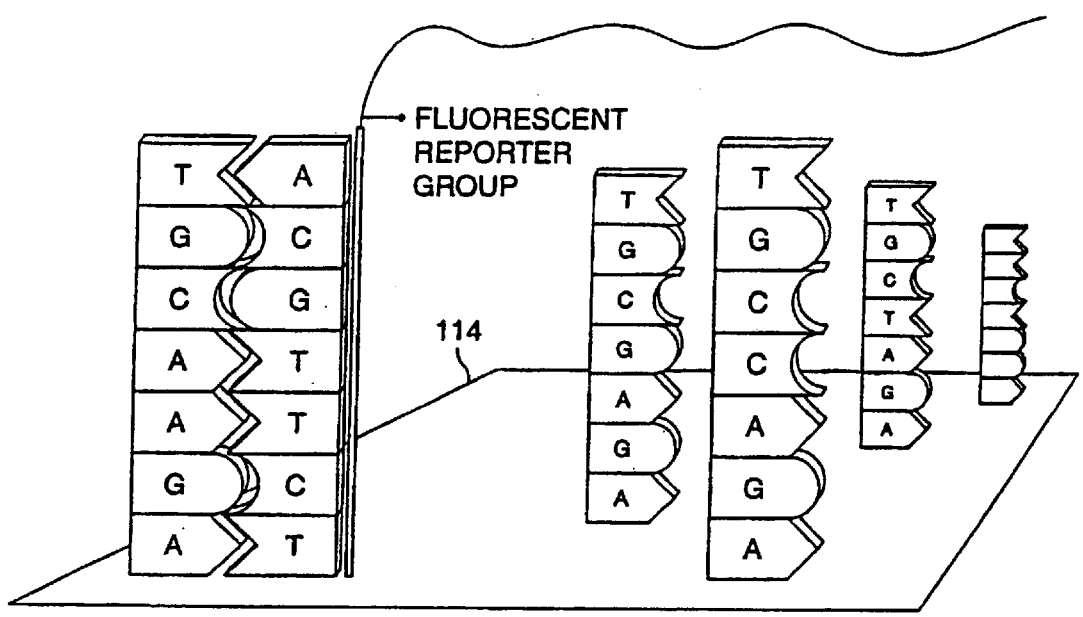
FIG. 6 illustrates conceptually the binding of nucleic acid probes on chips to a labeled target.
FIG. 7 illustrates nucleic acid probes arranged in lanes on a chip.
FIG. 8 illustrates a hybridization pattern of a target on a chip with a reference sequence as in FIG. 7.

FIG. 6 illustrates the binding of a particular target DNA to an array of DNA probes 114. As shown in this simple example, the following probes are formed in the array (only one probe is shown for the wild-type probe):

```
3'-AGAACGT
   AGACCGT
   AGAGCGT
   AGATCGT
      .
      .
      .
```

As shown, the set of probes differ by only one base, a single base mismatch at an interrogation position, so the probes are designed to determine the identity of the base at that location in the nucleic acid sequence. Accordingly, when used herein a unit will refer to multiple sets of related probes, where each set includes probes that differ by a single base mismatch at an interrogation position.

When a fluorescein-labeled (or otherwise marked) target with the sequence 5'-TCTTGCA is exposed to the array, it is complementary only to the probe 3'-AGAACGT, and fluorescein will be primarily found on the surface of the chip where 3'-AGAACGT is located. Thus, for each set of probes that differ by only one base, the image file will contain four fluorescence intensities, one for each probe. Each fluorescence intensity can therefore be associated with the nucleotide or base of each probe that is different from the other probes. Additionally, the image file will contain a "blank" cell that can be used as the fluorescence intensity of the background. By analyzing the fluorescence intensities associated with a specific base location, it becomes possible to extract sequence information from such arrays using the methods of the invention disclosed herein.

FIG. 7 illustrates probes arranged in lanes on a chip. A reference sequence (or chip wild-type sequence) is shown with five interrogation positions marked with number subscripts. An interrogation position is oftentimes a base position in the reference sequence where the target sequence may contain a mutation or otherwise differ from the reference sequence. The chip may contain five probe cells that correspond to each interrogation position. Each probe cell contains a set of probes that have a common base at the interrogation position. For example, at the first interrogation position, $I_1$, the reference sequence has a base T. The wild-type probe for this interrogation position is 3'-TGAC where the base A in the probe is complementary to the base at the interrogation position in the reference sequence.

Similarly, there are four "mutant" probe cells for the first interrogation position, $I_1$. The four "mutant" probes are 3'-TGAC, 3'-TGCC, 3'-TGGC, and 3'-TGTC. Each of the four "mutant" probes varies by a single base at the interrogation position. As shown, the wild-type and "mutant" probes are arranged in lanes on the chip. One of the "mutant" probes (in this case 3'-TGAC) is identical to the wild-type probe and therefore does not evidence a mutation. However, the redundancy may be utilized to give a visual indication of substitution mutations as will be seen in FIG. 8.

Still referring to FIG. 7, the chip contains wild-type and "mutant" probes for each of the other interrogation positions $I_2$–$I_5$. In each case, the wild-type probe is equivalent to one of the "mutant" probes.

FIG. 8 illustrates a hybridization pattern of a target on a chip with a reference sequence as in FIG. 7. The reference sequence is shown along the top of the chip for comparison. The chip includes a WT-lane (wild-type), an A-lane, a C-lane, a G-lane, and a T-lane (or U). Each lane is a row of cells containing probes. The cells in the WT-lane contain probes that are complementary to the reference sequence. The cells in the A-, C-, G-, and T-lanes contain probes that are complementary to the reference sequence except that the named base is at the interrogation position.

In one embodiment, the hybridization of probes in a cell is determined by the fluorescent intensity (e.g., photon counts) of the cell resulting from the binding of marked target sequences. The fluorescent intensity may vary greatly among cells. For simplicity, FIG. 8 shows a high degree of hybridization by a cell containing a darkened area. The WT-lane allows a simple visual indication that there is a mutation at interrogation position 14 because the wild-type cell is not dark at that position. The cell in the C-lane is darkened which indicates that the mutation is from T->G (the probes are complementary so the C-cell indicates a G mutation). In a preferred embodiment, the WT-Lane is not utilized so four cells (not including any "blank" cell) are utilized to call a base at an interrogation position.

In practice, the fluorescent intensities of cells near an interrogation position having a mutation are relatively dark creating "dark regions" around a mutation. The lower fluorescent intensities result because the cells at interrogation positions near a mutation do not contain probes that are perfectly complementary to the target sequence; thus, the hybridization of these probes with the target sequence is lower. For example, the relative intensity of the cells at interrogation positions $I_3$ and $I_5$ may be relatively low because none of the probes therein are complementary to the target sequence. Although the lower fluorescent intensities reduce the resolution of the data, the methods of the present invention provide highly accurate base calling within the dark regions around a mutation and are able to identify other mutations within these regions.

Figure 9:
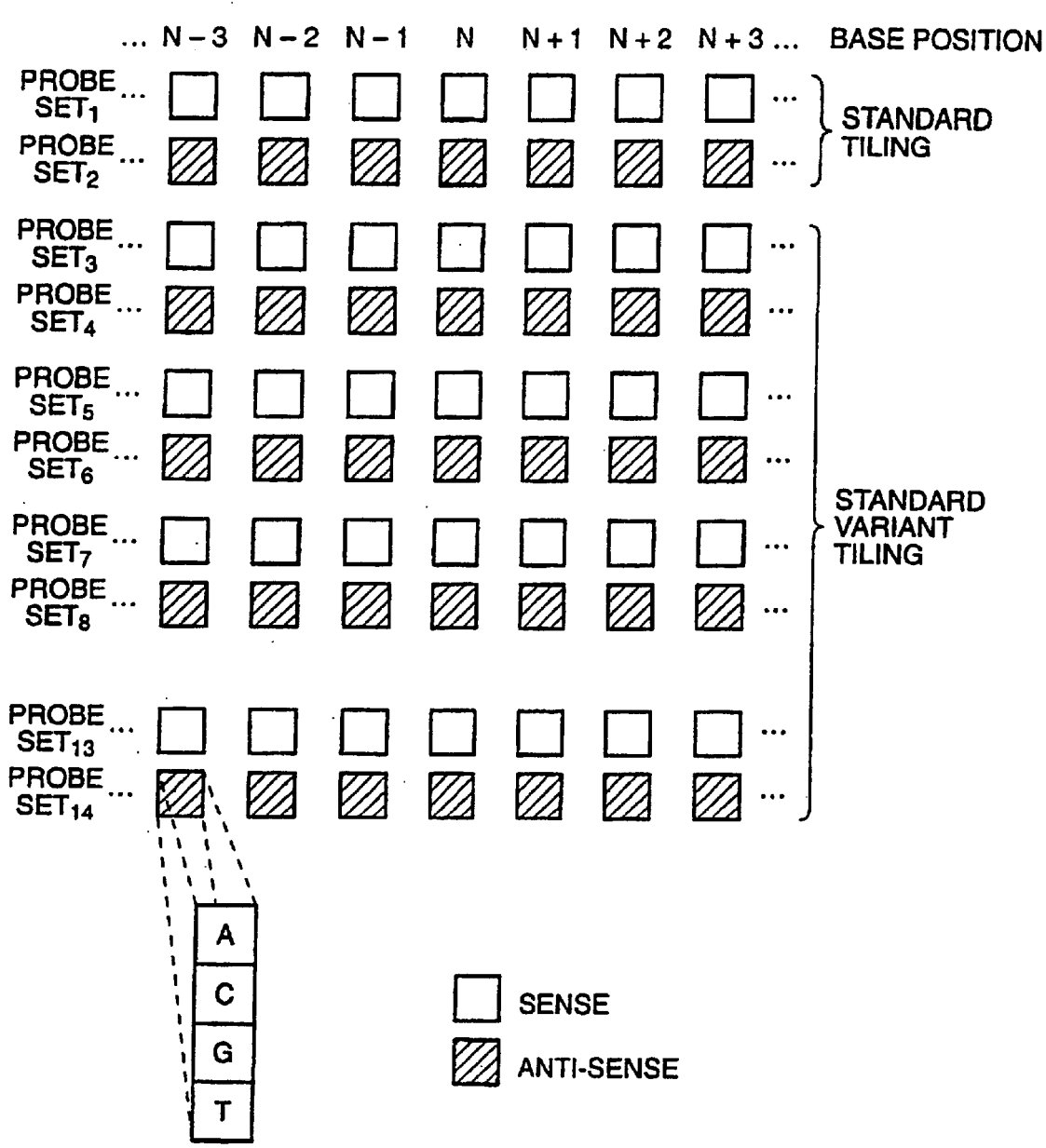
FIG. 9 illustrates standard and standard variant tilings.

FIG. 9 illustrates standard and standard variant tilings on a chip. As shown, the chip includes twelve probe sets (probe sets 1–14). The odd probe sets are include sense probes and the even probe sets (indicated by the cross hatching) include anti-sense probes. Probe sets 1 and 2 are tiled (i.e., designed and synthesized on the chip) to include probes complementary to the reference sequence, typically with a substitution position near the middle of the probe. In order to increase the accuracy of the analysis, preferred embodiments include standard variant tilings (shown as probe sets 3–14). Probes in the standard variant tilings are also complementary to the reference sequence; however, the probes have a substitution position and/or length that differs from the probes in the standard tiling. Each position may include one to six pairs of standard variant tiling probe sets, which may be varied accordingly to how likely it is believed that there may be a mutation at that position. Although twelve standard variant tiling probe sets are shown, the number may be varied as desired.

The expanded section at the bottom left portion of FIG. 9 illustrates that each block of a probe set typically includes four cells, denoted A, C, G, and T. The probe set may also include a cell for detecting deletion mutations (i.e., the interrogation position base is absent) and/or a "blank" cell for determining background intensity. The base designations specify which base is at the interrogation position of each probe within the cell. Typically, there are hundreds or thousands of identical nucleic probes within each cell.

Although in preferred embodiments the cells may be arranged adjacent to each other in sequential order along the reference sequence, there is no requirement that the cells be in any particular location as long as the location on the chip is determinable. Additionally, although it may be beneficial to synthesize the different groups on a single chip for consistency of experiments, the methods of the present invention may be advantageously utilized with data from different tilings on different chips.

Embodiments of the invention may be utilized to detect monomer changes in a heterogeneous sample when an unknown quantity of wild-type monomers may also be present. For example, mutations in the p53 gene have been identified as a potential prelude to some cancers. Tissue samples from a tumor will typically include a cellular mixture so it would be beneficial to identify mutations in the nucleic acid sequences of the mixture in the presence of wild-type nucleotides. The following will describe embodiments that analyze heterogeneous samples including nucleic acid sequences to detect mutations in the p53 gene. However, the invention is not limited to this application and may be advantageously applied to analyzing other genes and different types of sequences (e.g., peptides) as examples.

In order to detect mutations in a heterogeneous sample of nucleic acid sequences, embodiments of the invention compare the hybridization affinity between a homogeneous sample and a set of probes to the hybridization affinity between the heterogeneous sample and a set of probes. A homogeneous sample includes primarily one nucleic acid sequence (the reference sequence) or fragments thereof. There may be small concentrations of test sequences that have been added for quality control purposes, but the sample is considered to be homogeneous. The heterogeneous sample includes the reference sequence and mutations of that sequence, be it a substitution, deletion, insertion, or multiple base deletion.

Typically, the probes for analyzing the homogeneous and heterogeneous samples are the same, but this is not required. As discussed above, the homogeneous sample is utilized as a reference for analyzing the heterogeneous sample. The homogeneous and heterogeneous samples are preferably hybridized to probes on a chip under the same conditions. In preferred embodiments, the homogeneous sample includes wild-type nucleic acid sequences and the probes are tiled on a chip for these wild-type nucleic acid sequences.

Figure 10:
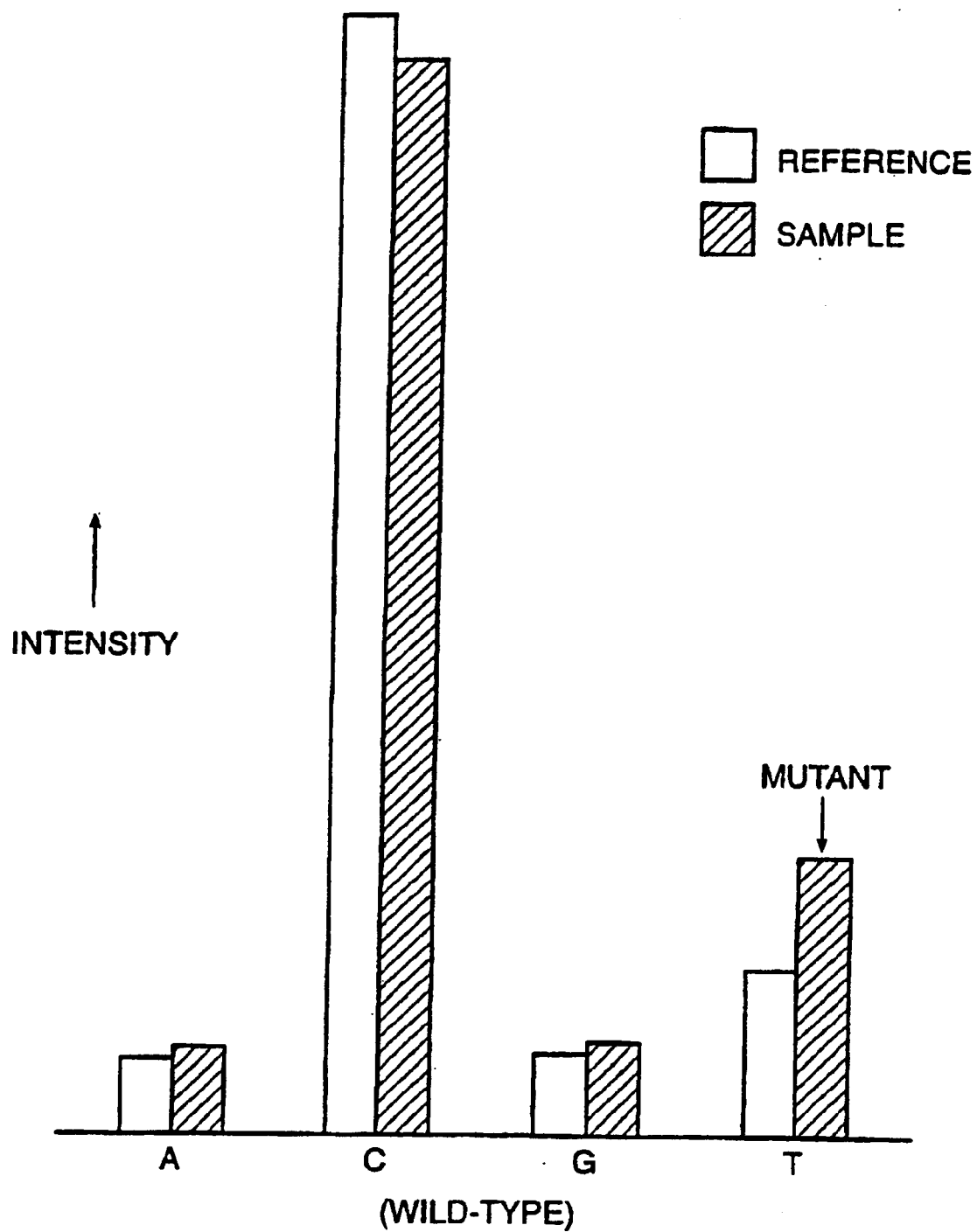
FIG. 10 shows a bar graph including hybridization affinity of a homogeneous sample and a heterogeneous sample.

In order to illustrate one process of detecting mutations, FIG. 10 shows a bar graph including hybridization affinity of a homogeneous sample (or "reference") and a heterogeneous sample (here designated as "sample"). In this example, the homogeneous sample includes sequences having a wild-type base at the position being analyzed so it is expected that the hybridization affinity of the reference sequences to the probe that includes the wild-type base would be highest. The bar graph shows that the hybridization affinity of the probes that includes the wild-type base (i.e., a C at this position) is by far the highest. The hybridization affinities shown are fairly typical and it should be noted that the hybridization affinities of the other probes are not zero. This may be due the specific interactions of the nucleotides, cross-hybridization or other reasons.

The shaded bars in FIG. 10 represent the hybridization affinity of an heterogeneous sample to the same probes. The heterogeneous sample includes nucleic acid sequences that are similar to the reference sequences, but there may be mutations present. As shown, the hybridization affinities of the heterogeneous sample are similar to the hybridization affinities of the homogeneous sample. However, the hybridization affinity of wild-type probe decreased slightly while the hybridization of the probe having a T at the interrogation position increased. This may indicate that some of the sample sequences have a mutation (i.e., a substitution to A since the probes are complementary to the sequences) at the position being analyzed.

Figure 11:
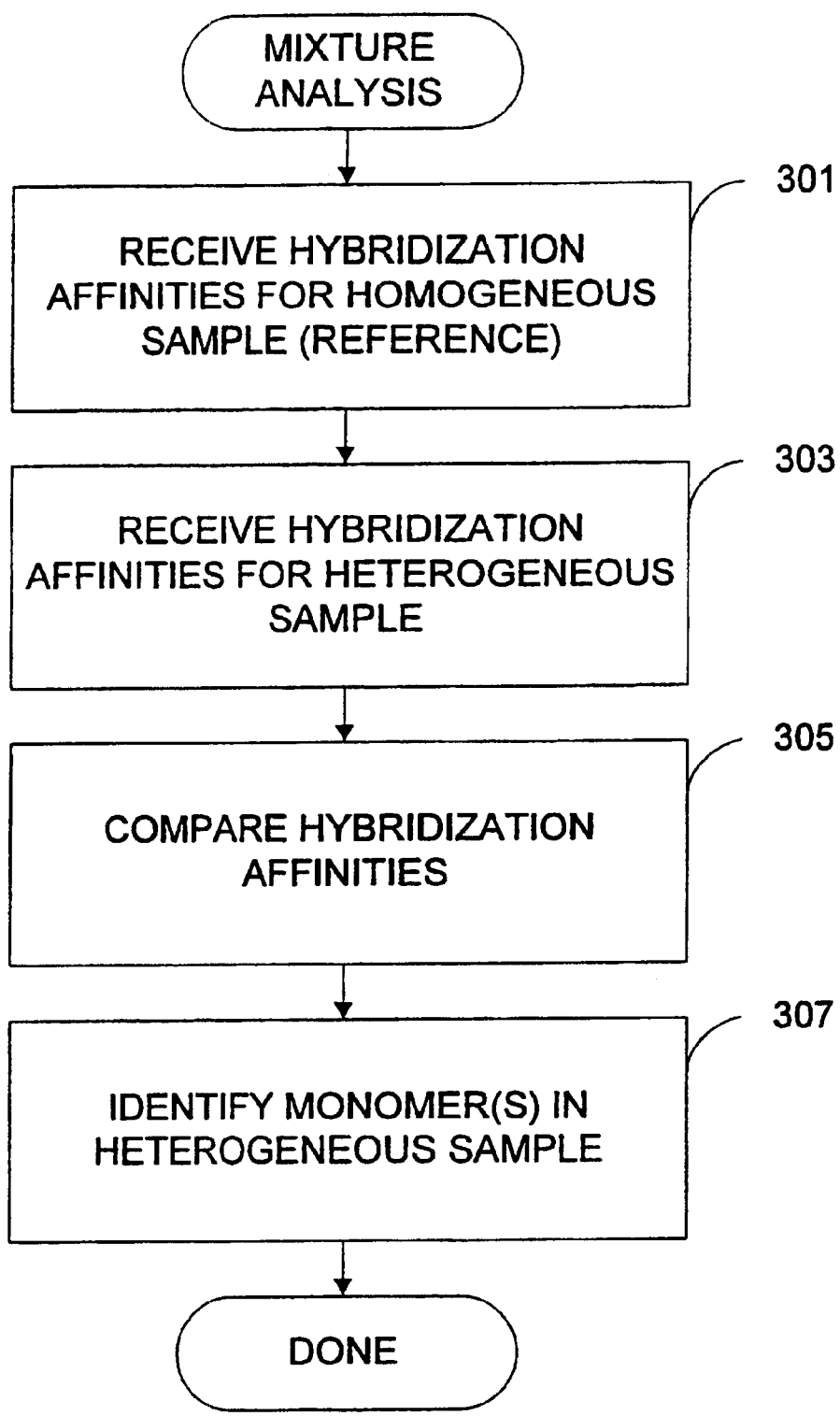
FIG. 11 shows a flowchart of a process that analyzes hybridization affinities for homogeneous and heterogeneous samples.

FIG. 11 shows a flowchart of a process that analyzes hybridization affinities for reference and heterogeneous samples, such as for the detection of mutations. The flowchart provides the high level flow of mixture analysis and specific details of preferred embodiments will be provided in the following figures and description. At a step 301, hybridization affinities for a homogeneous sample are received by a computer system. The hybridization affinities may be represented by photon counts from a fluorescein marker that are stored in a file. The file may be obtained by conventional mechanisms such as over a network or on a removable storage device (e.g., CD-ROM).

At a step 303, the computer system receives hybridization affinities for a heterogeneous sample. The hybridization affinities for the heterogeneous sample will typically be stored in a way similar to the hybridization affinities for the homogeneous sample. After the hybridization affinities for the reference and heterogeneous sample are received, the system compares the hybridization affinities of the reference and heterogeneous samples. There are many different ways that the hybridization affinities may be compared including the way described in reference to FIG. 10 (i.e., detecting a decrease in the wild-type probe affinity and an increase in a non-wild-type probe affinity in the heterogeneous sample). However, the details of other ways of comparing the hybridization affinities will be described in reference to later figures.

The system compares the hybridization affinities to identify the one or more monomers at a position in the sequences of the heterogeneous sample at a step 307. As an example, if the system detects a substitution mutation at a position, the system may indicate this to the user by "C/T," which means that a mutation to C was detected in the sample and the wild-type base is T. If the system does not detect a mutation, the system may indicate this to the user with a "T" for the wild-type base.

Figure 12:
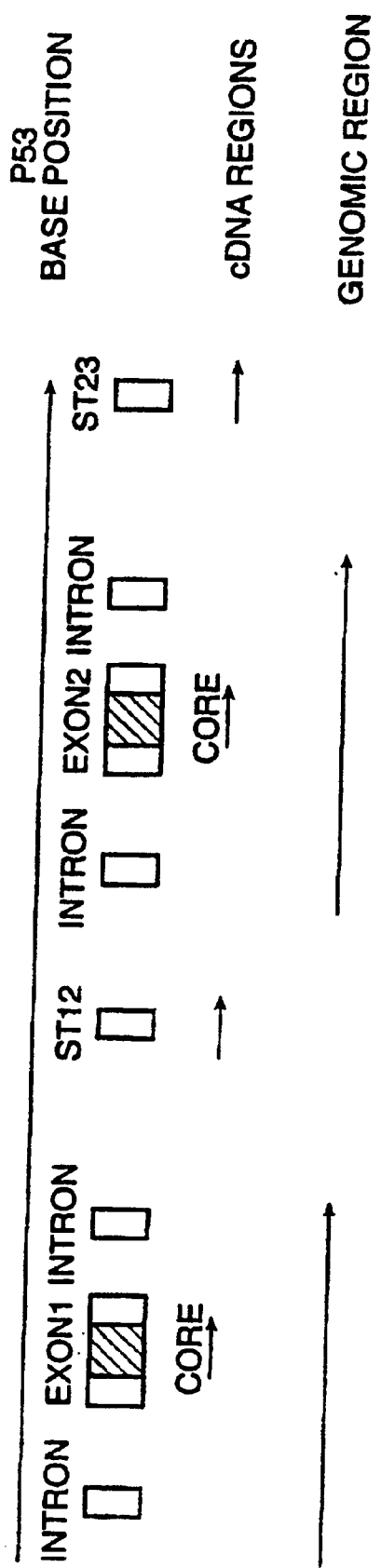
FIG. 12 shows a section of the p53 gene including intron, exon and splice junction regions.

Although the invention may be utilized in many applications, detecting mutations in the p53 gene of a heterogeneous sample will be described herein. FIG. 12 shows a section of the p53 gene. As shown, along the p53 gene are different regions including introns, exons and splice junctions. Chips may be designed that include probes for the cDNA regions (i.e., the exon cores and splice junctions), "genomic regions" between the introns, both, the whole gene, or any other parts of the gene. When analyzing the hybridization affinities, the system may determine if data for a region is acceptable. For simplicity, the following will describe checking data for an exon region. However, the region may be any region or set of regions on the gene.

Figure 13:
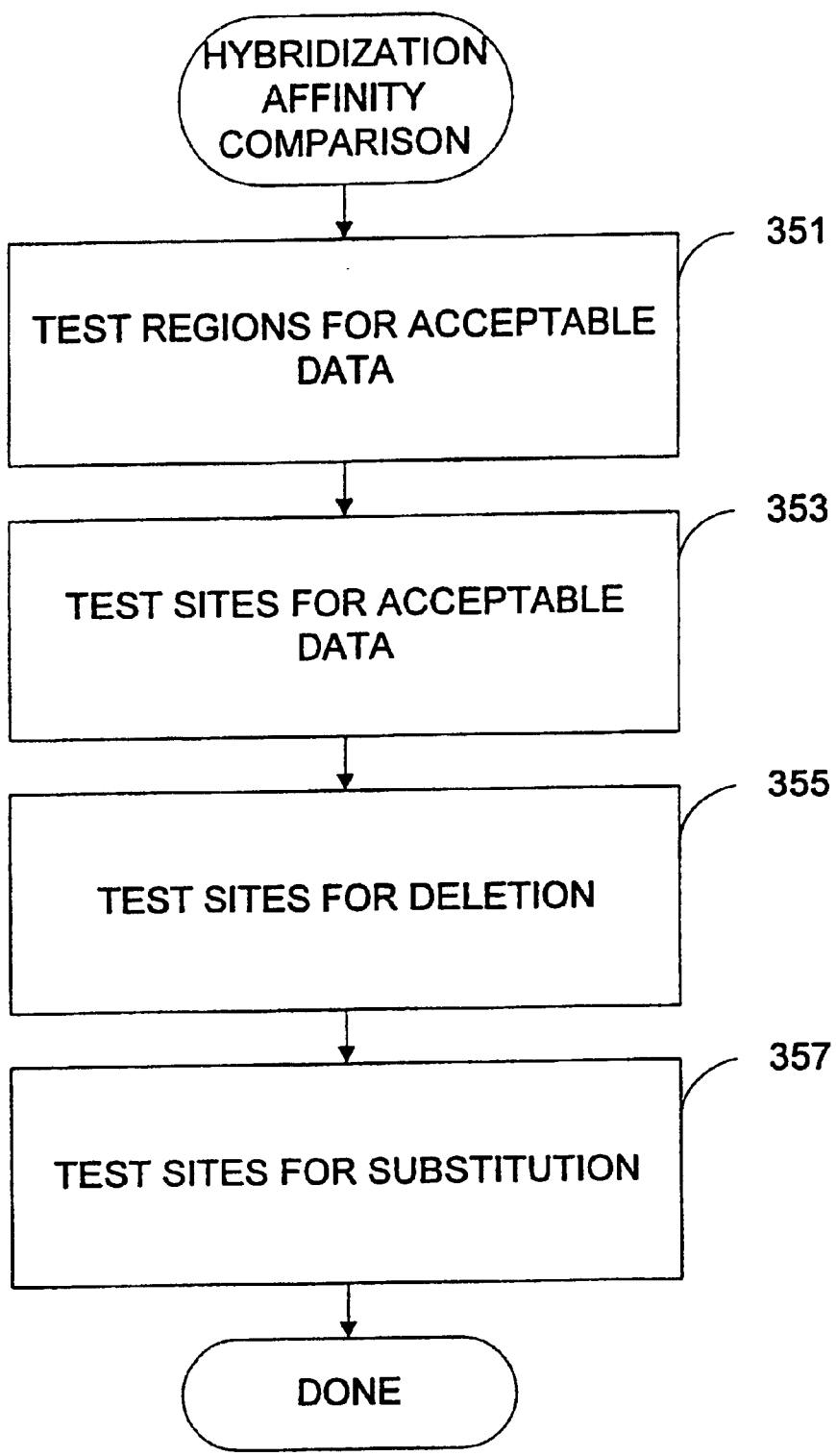
FIG. 13 shows a flowchart of a process of hybridization affinity comparison.

Now that a process of mixture analysis and chip design has been described, a process hybridization affinity comparison will be described. FIG. 13 shows a flowchart of a process of hybridization affinity analysis. The flowchart is one embodiment of step 305 of FIG. 11. At a step 351, the system tests regions for acceptable data. As discussed earlier, the regions may be exon regions. The system may determine if the hybridization affinities in a region are acceptable and if they are not, the system may not analyze any of the individual sites or positions in the region. For example, if more than a predetermined number of probe sets (see discussion of FIG. 9) do not have enough discrimination between wild-type probes and non-wild-type probes in the region, the system may deem the data for the region unacceptable.

At a step 453, the system tests the individual sites for acceptable data. For example, the system may subtract a background intensity (e.g., derived from a "blank" probe) from each of the intensities for each probe of a probe set. If the background subtracted intensities of the probes are not all above a minimum threshold, the system may deem the data from the probes in the probe set are unacceptable.

If the region has been determined to have acceptable data and some data at a site is deemed acceptable, the system can perform a test for a deletion at a step 355. In order to test for a deletion, a probe is synthesized on the chip that would be complementary to a deletion. For example, referring back to FIG. 7, the four probes are 3'-TGAC, 3'-TGCC, 3'-TGGC, and 3'-TGTC, where the interrogation position is underlined. In order to test for a deletion at this interrogation position, a probe 3'-TGC is synthesized on the chip. In practice, the lengths of the probes are typically longer (e.g., 12-mers to 15-mers), but the shorter probes are used herein for illustrative purposes.

Each probe set at a site or position is analyzed to determine if the probe set indicates that there has been a deletion mutation at this position. If the number of probe sets that indicate there has been a deletion exceeds a threshold, the system may indicate that there has been a deletion at this position.

At a step 457, the system performs a test for a substitution. Assuming the region has been determined to have acceptable data and some data at the site is deemed acceptable, the system analyzes the hybridization affinities of the probes of each probe set to determine if the probe set indicates that there was a substitution mutation. If more than a predetermined number of probe sets agree that there has been a substitution, the system may indicate that there has been a substitution at this position.

The probe sets can include probes to test for other mutations including insertions and multiple-base deletions. Accordingly, the flowchart of FIG. 13 can include steps for testing sites for insertions, multiple base deletions, and the like. Insertion mutations are detected by analyzing probe sets that have been tiled on the chip for detecting an insertion at a specific position. For example, there may be four insertion probes that include a different base that has been added between two adjacent bases in the reference sequence. A determination of whether there has been an insertion may be based on whether a predetermined number of probe sets agree that there has been an insertion. Multiple base deletion probes are similar to the single deletion probe described above except that more than one base has been deleted. Chips can be synthesized that include probes for deletions, insertions and multiple base deletions for each site or only at designated sites.

The preceding description has described the invention but it may be beneficial to describe a preferred embodiment of the invention in detail. FIGS. 20A–20G show formulas that are utilized in a preferred embodiment. These formulas will be described in reference to flowcharts that illustrate this embodiment. Unless otherwise indicated, the hybridization intensities of the probes are background subtracted.

Figure 14:
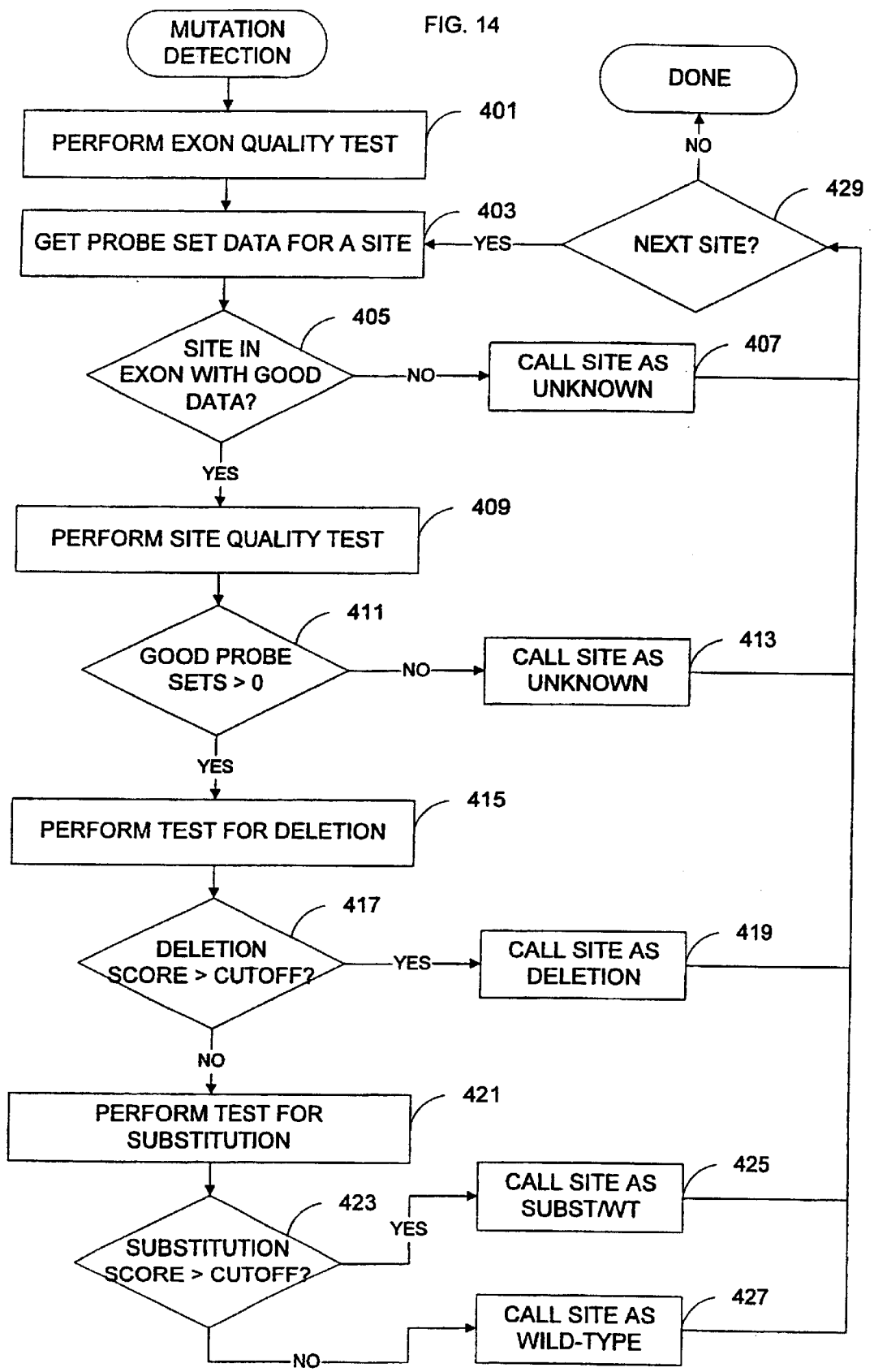
FIG. 14 shows a flowchart of a process of mutation detection in a heterogeneous sample of nucleic acids.

FIG. 14 shows a flowchart of a process of mutation detection in a heterogeneous sample of nucleic acids. The flowchart begins after the relevant hybridization affinity data has been input into the system. The hybridization affinity data includes the probe sequence and the hybridization affinity (or intensity) for the probe, which may be calculated as the mean of the photon counts from a cell that includes the probe. In preferred embodiments, the hybridization affinity data for the reference and heterogeneous samples were obtained under the same conditions.

For simplicity, the flowchart will describe a process of detecting mutations in the multiple sites of an exon. It should be readily understood that the process may be extended to analyze multiple exons or different regions altogether.

At a step 401, the system performs an exon quality test. The purpose of the exon quality test is to detect and eliminate from analysis an exon that has hybridization affinity data that will likely have a high error rate. The exon quality test the degree to which hybridization intensity values discriminate between the wild-type probe and the three non-wild-type probes in a probe set. It has been determined that less discrimination results in higher error rates for the exon and it may be that the error rate increases exponentially with decreasing discrimination.

With the exon quality test, a DiscQualityFilter value is calculated (see FIG. 20C). In order to calculate the DiscQualityFilter value, a ratio of the hybridization affinity of the wildtype probe to the average of the hybridization affinities of the non-wild-type probes is calculated for each probe set. The average of the ratios for each probe set is calculated to produce the DiscQualityFilter value. Probe sets that include one or more probes that have a hybridization affinity lower than a background intensity may be excluded from calculating the DiscQualityFilter value.

In general, the higher the DiscQualityFilter value, the lower the error rates for the exon are expected. For each exon, the DiscQualityFilter value is compared to an ExonIntDiscCutoff value and if the DiscQualityFilter value is less than the ExonIntDiscCutoff value, the hybridization affinity data for the exon fails and is deemed unacceptable. Otherwise, the hybridization affinity data for the exon is deemed acceptable. Each exon may have a different ExonIntDiscCutoff value, which may be determined empirically.

At a step 403, the system gets probe set data for a site. It is then determined if the site is located in an exon with acceptable data at a step 405. The determination of whether the exon has acceptable hybridization affinity data was calculated at step 401, which would typically perform the exon quality test for all the exons of interest. If the probe set is for a site that is located in an exon with unacceptable data, the site is called as unknown or "N."

Otherwise, if the probe set is for a site that is located in an exon with acceptable data, the system performs a site quality test at a step 409. The purpose of the site quality test is to remove probe sets that do not have acceptable data quality from the site calculation. If a probe set for the homogeneous sample is deemed to have unacceptable data, the corresponding probe set for the heterogeneous sample is also removed, and vice versa.

Probe sets will be removed from analysis of the reference and heterogeneous samples by the site quality test if any one of four conditions is true. The first condition is if RefMaxInt is less than IntCutoff. UKMaxInt is the maximum hybridization intensity of a probe in the reference probe set (see FIG. 20C). If this maximum is less than a predetermined threshold IntCutoff, then the probe sets are removed. The second condition is if UKMaxInt is less than IntCutoff UKMaxInt is similar to RefMaxInt and is the maximum hybridization intensity of a probe in the sample probe set. If this maximum is less than IntCutoff, then the probe sets are removed.

The third condition is if RefIntDisc is less than MinIntDisc. This condition tests the intensity discrimination of the reference probe set. The RefIntDisc value is the ratio of the raw hybridization affinity of the wild-type probe (i.e., not background subtracted) to the average of the raw hybridization affinities of the non-wild-type probes. If RefIntDisc is less than a predetermined MinIntDisc, then the probe sets are removed. The fourth condition is if VectorRatio is greater than MaxVectorRatio, which is a predetermined value. This condition tests whether the magnitude of the vector formed by the four hybridization intensities of the probe set do not differ above a threshold between the reference and unknown (see FIGS. 20B and 20C). If VectorRatio is greater than Max VectorRatio, then the probe sets are removed.

After the site quality test is performed, it is determined if the number of probe sets remaining is greater than zero at a step 411. If not, the site is called an unknown or "N" at a step 413. Otherwise, the system performs a test for a deletion mutation at a step 415. The test for a deletion mutation is shown in more detail in FIG. 15.

Figure 15:
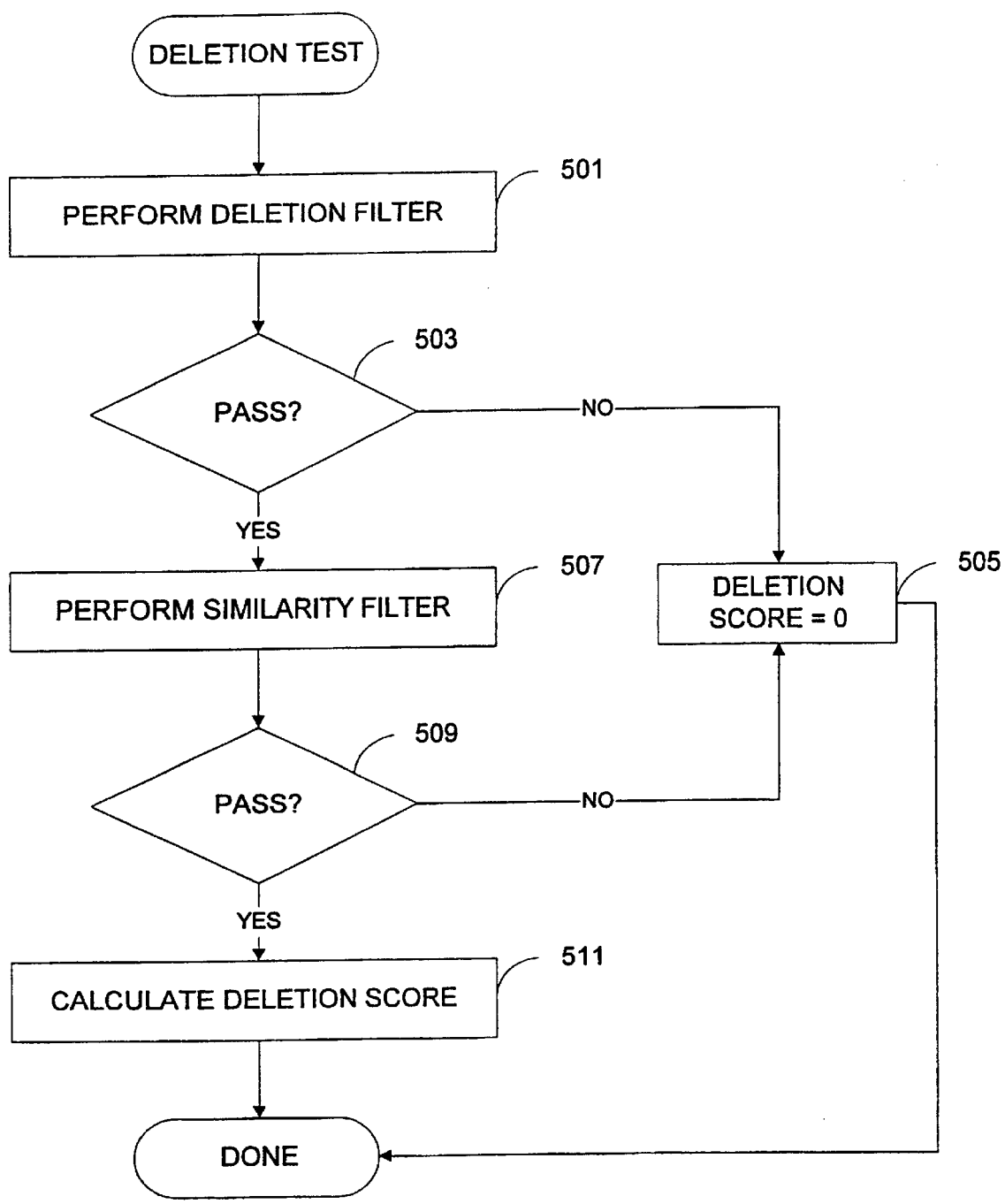
FIG. 15 shows a flowchart of a process of testing for a deletion mutation.

FIG. 15 shows a flowchart of a process of testing for a deletion mutation. At a step 501, a deletion filter is performed. The deletion filter calculates a delRatio for each probe set that passed the site quality test. The calculation for delRatio is shown in FIG. 20C and if the value is greater than zero, the probe set indicates that there is a deletion. If the number of probe sets that make a deletion mutant call with the deletion filter does not exceed a predetermined threshold at a step 503, the site is given a deletion score of zero at a step 505, meaning that a deletion mutation has not been indicated and the site will be tested for a substitution mutation. Otherwise, the similarity filter is performed at a step 507.

The similarity filter tests whether any of the sample probe sets have the "same" intensity pattern as that of any of the reference probe sets. The rational is that random experimental variation may cause differences in the intensity patterns. Therefore, it would be a nonrandom event if both the reference and sample probes sets have a very nearly identical hybridization pattern. Such an event would likely only be caused by a wild-type base at the interrogation position. The test for the same hybridization pattern may be computed by a dot vector between the four reference intensities and the four sample intensities. If the similarity of any of the probe set pairs is greater than a cutoff, the site does not pass the similarity filter at a step 509 and will be tested for a substitution mutation (by setting the deletion score to zero at a step 505). In preferred embodiments, the hybridization intensity patterns should be very near identical before they fail the similarity filter.

At a step 511, the system calculates a deletion score. The deletion score for each probe set is the sum of two "mixture variables": dot metric and dRatio. The dot metric is correlated with increasing differences in the probe set intensities of the sample relative to the reference, but does not quantitate any specific pattern of differences (see FIG. 20E). The dRatio variable is correlated with the degree to which a non-wild-type probe intensity increases while the wild-type probe intensity decreases in the sample, relative to the reference (see FIG. 20E). The sum of dot metric and dRatio is the deletion score, in which generally a higher deletion score indicates a greater likelihood of a deletion mutation.

Returning to FIG. 14, the deletion score is compared to a deletion cutoff at a step 417. If the deletion score is greater than the deletion cutoff, the site is called as a deletion at a step 419. For example, the site may be called as "-/T," where the dash indicates a deletion and the T indicates the wild-type base. In a preferred embodiment, the deletion cutoff varies depending on the number of probe sets that pass the site quality test.

If the deletion score is not greater than the deletion cutoff at step 417, the system performs a test for a substitution mutation at a step 421. The test for a substitution mutation is shown in more detail in FIG. 16.

Figure 16:
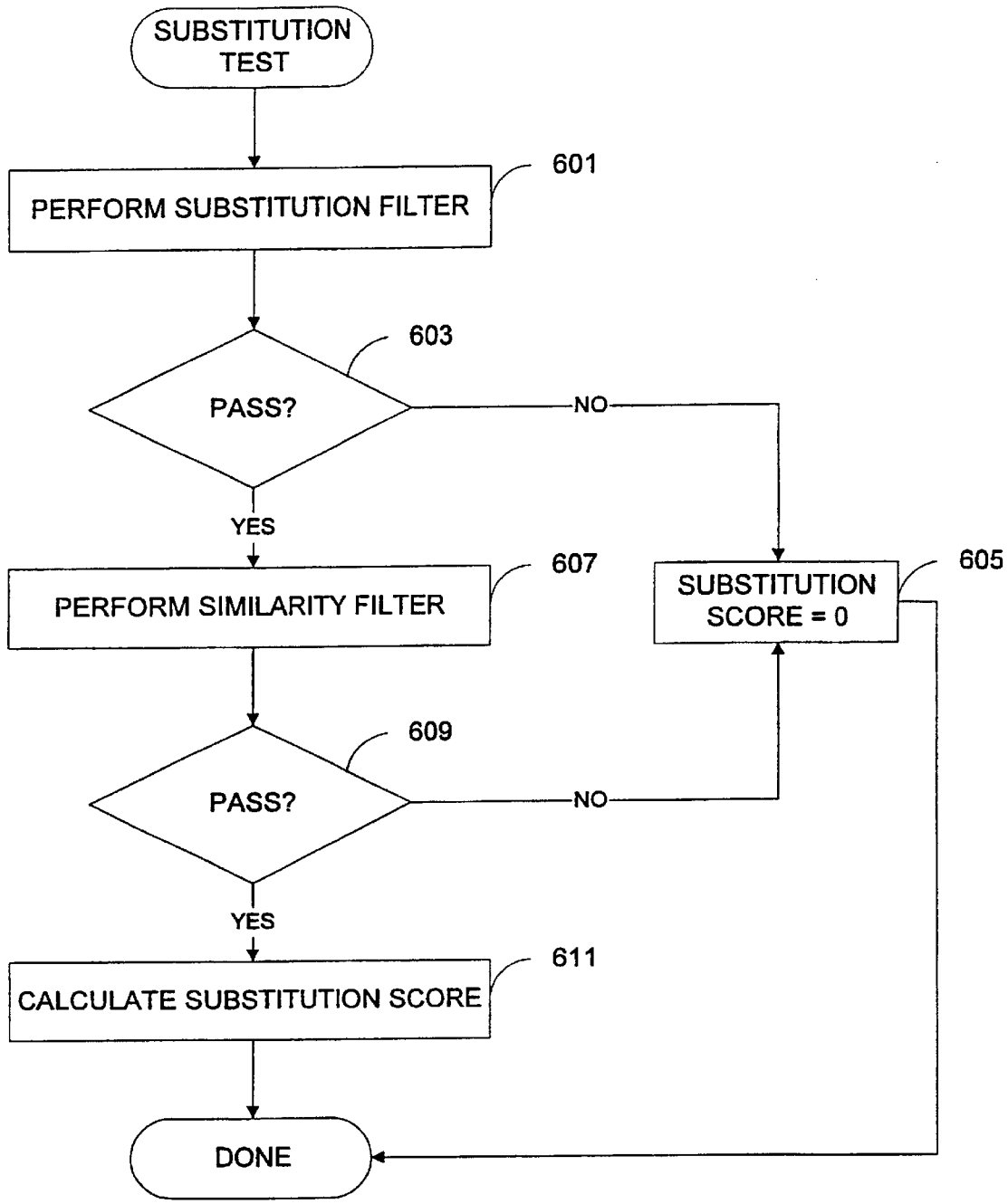
FIG. 16 shows a flowchart of a process of testing for a substitution mutation.
Figure 17:
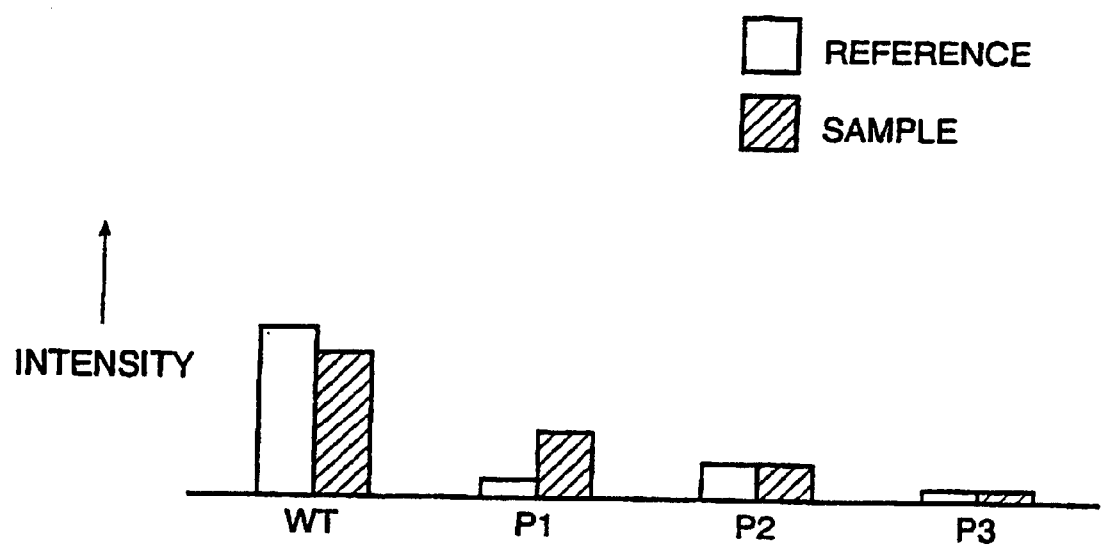
FIG. 17 shows homogeneous and homogeneous sample probe set intensities.

FIG. 16 shows a flowchart of a process of testing for a substitution mutation. At a step 601, a substitution filter is performed. The substitution filter produces three ratios for each probe set that passed the site quality test. Each of the three ratios is produced by dividing the wild-type probe intensity by a non-wild-type probe intensity. For example, FIG. 17 shows reference and sample probe set intensities. The wild-type probe intensity is designed "WT" and the non-wild-type probe intensities are designate "P1," "P2" and "P3." The ratios WT/P1, WT/P2 and WT/P3 are calculated for each probe set.

When the fraction of non-wild-type base relative to wild-type base at a site increases, the intensity of one of the non-wild-type probes increases while the intensity of the wild-type probe decreases. Therefore, the presence of a substitution mutation will typically decrease one of the three ratios for the sample relative to the same ratio for the reference. A probe set may indicate that the base specified by the non-wild-type probe with the greatest decrease (if any) in the ratios if the probe set also passes tests for the "shape" of the intensity pattern differences as described in reference to FIG. 18.

Figure 18:
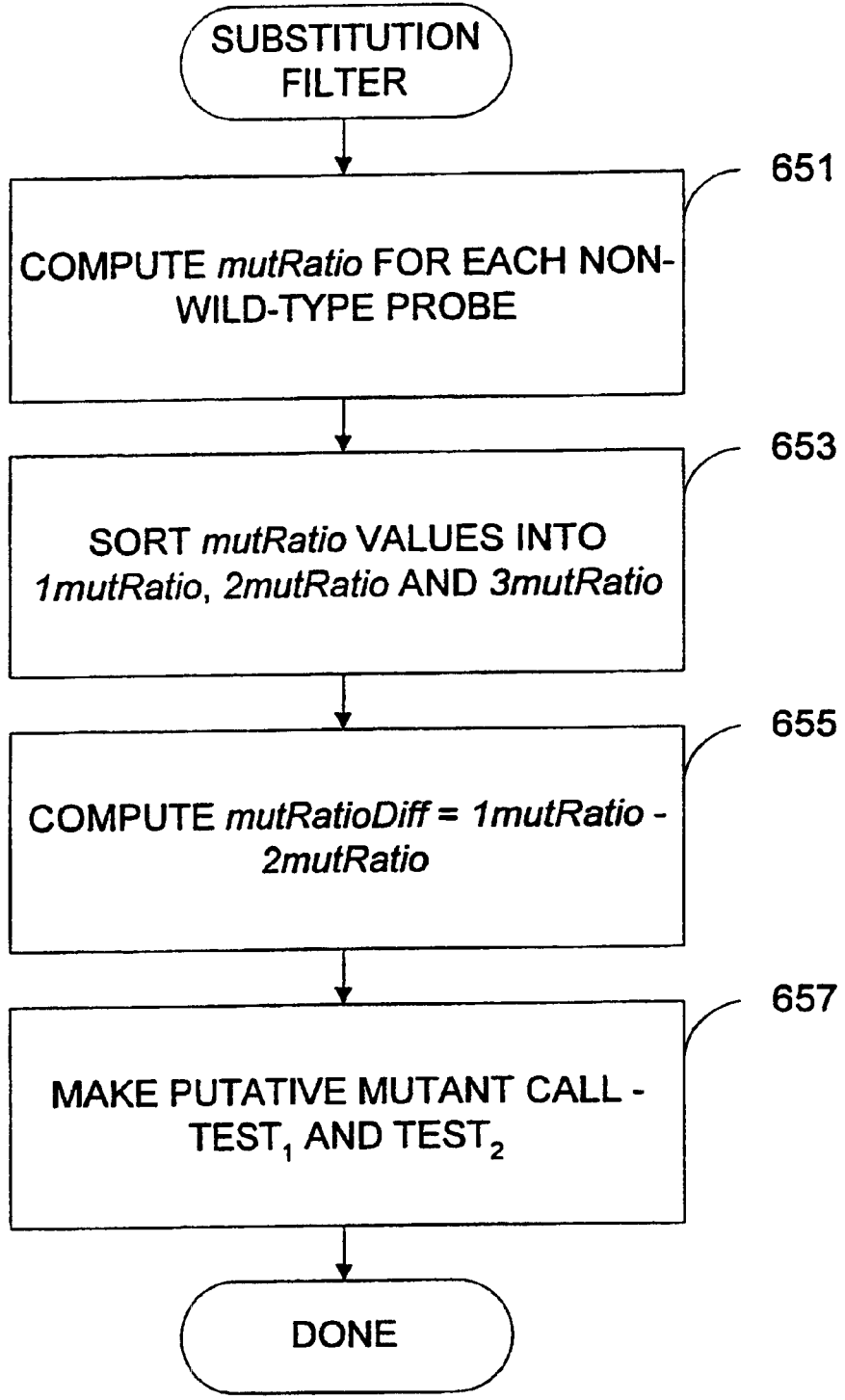
FIG. 18 shows a flowchart of a process of a substitution filter.

FIG. 18 shows a flowchart of a process of a substitution filter. At a step 651, the system computes a mutRatio for each non-wild-type probe. The mutRatio is a ratio of wild-type and non-wild-type intensities from the reference and sample (see FIG. 20C). The higher the value, the more likely there is a substitution mutation.

At a step 653, the system sorts the three mutRatio values in descending order and rename the values so that 1mutRatio>2mutRatio>3mutRatio (i.e., 1mutRatio is the highest value). The system then calculates the mutRatioDiff at a step 655, which is the difference between 1mutRatio and 2mutRatio. There are two tests performed at a step 657 to make a putative base call. If either test is passed, the probe set indicates that the site is a substitution mutation. The two tests, $Test_1$, and $Test_2$, are shown in FIG. 20G. In general, $Test_1$ requires more probe sets to agree on the call but has a less stringent "shape" requirement to call a putative mutant call than $Test_2$. If both tests fail, the probe set is treated as indicating that the site is wild-type.

If the number of probe sets that make a substitution mutant call with the substitution filter does not exceed a predetermined threshold at a step 603, the site is given a substitution score of zero at a step 605, meaning the site will be called as wild-type. Otherwise, the similarity filter is performed at a step 607.

The similarity filter tests whether any of the sample probe sets have the "same" intensity pattern as that of any of the reference probe sets. The similarity filter may be the same as described in reference to step 507 in FIG. 15. If the similarity of any of the probe set pairs is greater than a cutoff, the site does not pass the similarity filter at a step 609 and will be called as wild-type (by setting the substitution score to zero at step 605). As mentioned earlier, in preferred embodiments, the hybridization intensity patterns should be very near identical before they fail the similarity filter.

At a step 611, the system calculates a substitution score. The substitution score for each probe set is the sum of four "mixture variables": dot metric, dRatio, DneighborRatio, and rank. The dot metric is correlated with increasing differences in the probe set intensities of the sample relative to the reference, but does not quantitate any specific pattern of differences (see FIG. 20E). The dRatio variable is correlated with the degree to which a non-wild-type probe intensity increases while the wild-type probe intensity decreases in the sample, relative to the reference (see FIG. 20E).

The DNeighborRatio variable is correlated with the degree to which the intensities of neighboring probe sets decrease, relative to the reference (see FIG. 20F). The rank variable is a binary metric which is set to 1 when the highest intensity probe in the sample is not the same as the highest intensity probe in the reference (see FIG. 20F). The sum of dot metric, dRatio, DNeighborRatio, and rank is the substitution score, in which generally a higher substitution score indicates a greater likelihood of a substitution mutation.

Returning to FIG. 14, the substitution score is compared to a substitution cutoff at a step 423. If the substitution score is greater than the substitution cutoff, the site is called as a substitution at a step 425. For example, the site may be called as "G/A," where the indicates G the substitution mutation and the A indicates the wild-type base. In a preferred embodiment, the substitution cutoff varies depending on the number of probe sets that pass the site quality test.

Figure 19:
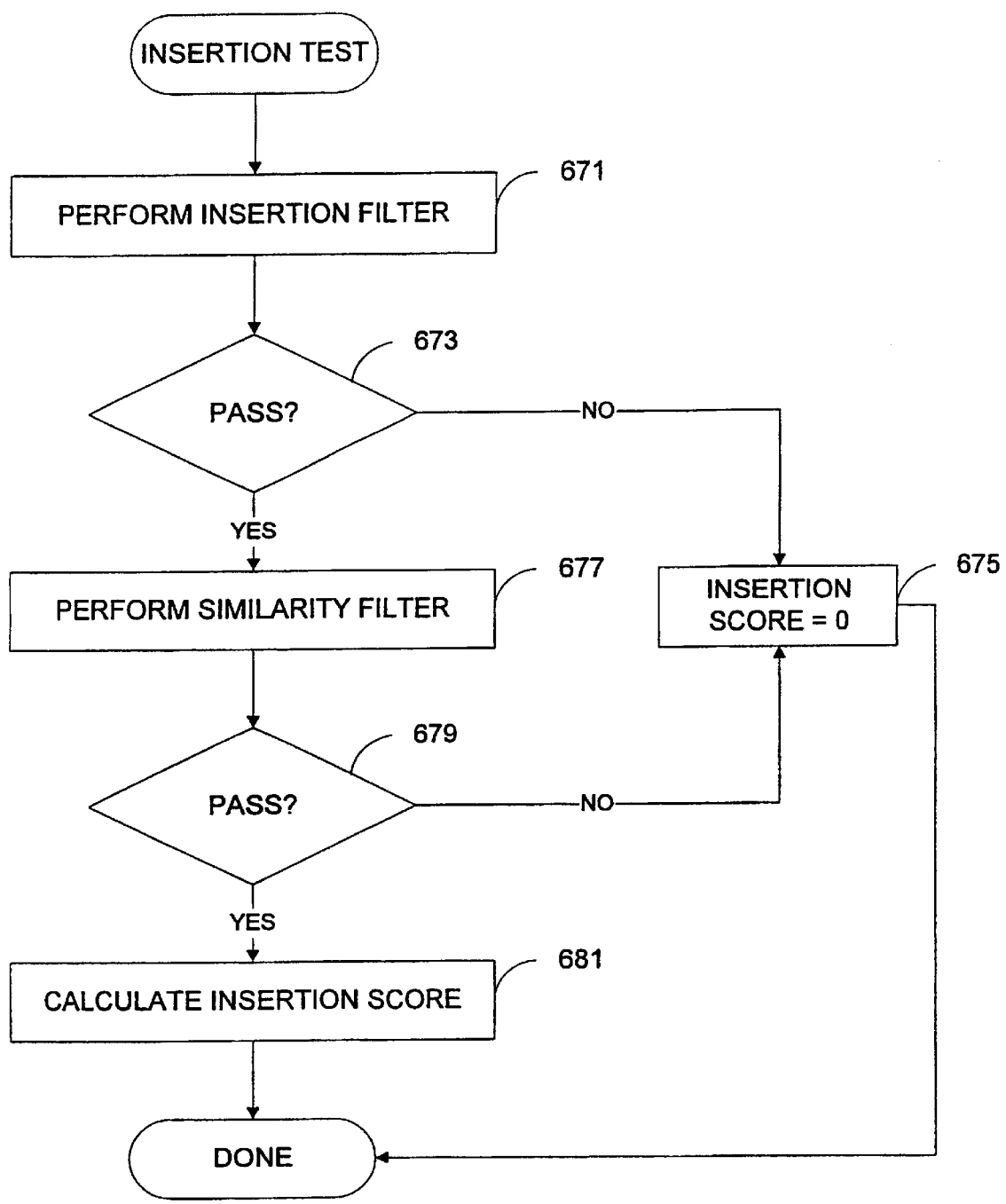
FIG. 19 shows a flowchart of a process of testing for a substitution mutation.

Although not shown in FIG. 14, a system can test for other mutations including insertions and multiple base deletions. The flowcharts for these mutation conditions may be similar to the ones already shown but FIG. 19 shows a flowchart of a process of testing for a insertion mutation.

At a step 671, an insertion filter is performed. The insertion filter calculates four ratios for each probe set that passed the site quality test. The calculation for each ratio is the same as the ratios described in reference to FIG. 17 except that four ratios WT/I1, WT/I2, WT/I3, and WT/I4, where I1–I4 represent the four insertion probes, are calculated. The presence of an insertion will typically increase on the four ratios for the sample relative to the same ratio for the reference. If the number of probe sets that make an insertion mutant call with the insertion filter does not exceed a predetermined threshold at a step 673, the site is given an insertion score of zero at a step 675, meaning that an insertion mutation has not been indicated.

A similarity filter is performed at a step 677. The similarity filter can be the same as described in reference to step 507 of FIG. 15. If the similarity of any of the probe set pairs is greater than a cutoff, the site does not pass the similarity filter at a step 679 and will be called as wild-type (by setting the insertion score to zero at step 675).

At a step 681, the system calculates an insertion score. The deletion score for each probe set is the sum of three "mixture variables": dot metric, dRatio and dNeighborRatio. The dot metric is correlated with increasing differences in the probe set intensities of the sample relative to the reference, but does not quantitate any specific pattern of differences (see FIG. 20E). The dRatio variable is correlated with the degree to which a non-wild-type probe intensity increases while the wild-type probe intensity decreases in the sample, relative to the reference (see FIG. 20E). The DNeighborRatio variable is correlated with the degree to which the intensities of neighboring probe sets decrease, relative to the reference (see FIG. 20F). The sum of dot metric, dRatio and dNeighborRatio is the insertion score, in which generally a higher insertion score indicates a greater likelihood of an insertion mutation.

With the present invention, mutations may be detected in a mixture of nucleic acid sequences in the presence of an unknown quantity of wild-type bases. Although the above description has described preferred embodiments, many variations of the invention will become apparent to those of skill in the art upon review of this disclosure. Merely by way of example, while the invention is illustrated primarily with regard to nucleic acid sequences, the invention may be advantageously applied to other polymers. The scope of the invention should, therefore, be determined not with reference to the above description, but instead should be determined with reference to the appended claims along with their fall scope of equivalents.

What is claimed is:

1. A method of analyzing a heterogeneous sample of nucleic acids, comprising:

receiving hybridization affinity data of a homogeneous sample of nucleic acids to a plurality of nucleic acid probes, the plurality of nucleic acid probes having different nucleotides at an interrogation position and including a wild-type probe and at least one non-wild-type probe;

receiving hybridization affinity data of a heterogeneous sample of nucleic acids to the plurality of nucleic acid probes;

calculating a first ratio of a hybridization affinity datum of a wild-type probe to a hybridization affinity datum of a non-wild-type probe for the homogeneous sample of nucleic acids;

calculating a second ratio of a hybridization affinity datum of a wild-type probe to a hybridization affinity datum of a non-wild-type probe for the heterogeneous sample of nucleic acids;

calculating a third ratio of the difference between the first and second ratios to the first ratio; and determining there is a mutation in the heterogeneous sample if the third ratio is above a predetermined threshold, the mutation being identified by the nucleotide at the interrogation position of the non-wild-type probe.

2. The method of claim 1, wherein the mutation is a substitution, deletion or insertion.

3. The method of claim 1, further comprising testing a region of the nucleic acids for acceptable data.

4. The method of claim 1, further comprising testing sites of the nucleic acids for acceptable data.

5. A computer program product for analyzing a heterogeneous sample of nucleic acids, comprising:

computer code that receives hybridization affinity data of a homogeneous sample of nucleic acids to a plurality of nucleic acid probes, the plurality of nucleic acid probes having different nucleotides at an interrogation position and including a wild-type probe and at least one non-wild-type probe;

computer code that receives hybridization affinity data of a heterogeneous sample of nucleic acids to the plurality of nucleic acid probes;

computer code that calculates a first ratio of a hybridization affinity datum of a wild-type probe to a hybridization affinity datum of a non-wild-type probe for the homogeneous sample of nucleic acids;

computer code that calculates a second ratio of a hybridization affinity datum of a wild-type probe to a hybridization affinity datum of a non-wild-type probe for the heterogeneous sample of nucleic acids;

computer code that calculates a third ratio of the difference between the first and second ratios to the first ratio;

computer code that determines there is a mutation in the heterogeneous sample if the third ratio is above a predetermined threshold, the mutation being identified by the nucleotide at the interrogation position of the non-wild-type probe; and a computer readable medium that stores the computer codes.

6. The computer program product of claim 5, wherein the computer readable medium is a floppy, tape, CD-ROM, hard drive, or flash memory.

7. The computer program product of claim 5, wherein the mutation is a substitution, deletion or insertion.

8. The computer program product of claim 5, further comprising computer code that tests a region of the nucleic acids for acceptable data.

9. The computer program product of claim 5, further comprising computer code that tests sites of the nucleic acids for acceptable data.

* * * * *